US011478252B2

(12) United States Patent
Mujawar

(10) Patent No.: US 11,478,252 B2
(45) Date of Patent: Oct. 25, 2022

(54) ENDOSCOPIC REPOSABLE SURGICAL CLIP APPLIER

(71) Applicant: Covidien LP, Mansfield, MA (US)

(72) Inventor: Arifmohamad Mujawar, Maharashtra (IN)

(73) Assignee: COVIDIEN LP, Mansfield, MA (US)

( * ) Notice: Subject to any disclaimer, the term of this patent is extended or adjusted under 35 U.S.C. 154(b) by 257 days.

(21) Appl. No.: 16/781,090

(22) Filed: Feb. 4, 2020

(65) Prior Publication Data

US 2020/0170646 A1 Jun. 4, 2020

Related U.S. Application Data

(63) Continuation of application No. 15/437,059, filed on Feb. 20, 2017, now Pat. No. 10,582,931.

(30) Foreign Application Priority Data

Feb. 24, 2016 (IN) .............................. 201621006379

(51) Int. Cl.
*A61B 17/128* (2006.01)
*A61B 17/122* (2006.01)
(Continued)

(52) U.S. Cl.
CPC ........ *A61B 17/1285* (2013.01); *A61B 17/122* (2013.01); *A61B 2017/0023* (2013.01);
(Continued)

(58) Field of Classification Search
CPC ....... A61B 17/128–1285; A61B 17/122–1227; A61B 17/10–105; A61B 17/083; A61B 2090/0803
See application file for complete search history.

(56) References Cited

U.S. PATENT DOCUMENTS 3,120,230 A 2/1964 Skold
3,363,628 A 1/1968 Wood
(Continued)

FOREIGN PATENT DOCUMENTS

AU 2013254887 A1 11/2013
CA 1163889 A 3/1984
(Continued)

OTHER PUBLICATIONS

Canadian Office Action corresponding to counterpart Int'l Application No. CA 2,676,211 dated Nov. 24, 2015.
(Continued)

*Primary Examiner* — Robert A Lynch
*Assistant Examiner* — Brigid K Byrd

(57) ABSTRACT

A clip cartridge assembly for use with a reposable surgical clip applier includes a clip tray, a plurality of surgical clips, and a cover. The clip tray includes a plurality of distally oriented, deflectable, resilient fingers projecting from a base wall thereof. Each resilient finger terminates in a distal shoulder and a proximal end of the clip tray is configured for selective connection with a clip pusher bar of an endoscopic assembly of the reposable surgical clip applier. The cover includes a plurality of distally oriented, deflectable, resilient fingers projecting within a channel defined through proximal and distal ends thereof. Each resilient finger of the cover terminates in a distal shoulder and the cover includes a pair of opposed slots defined within sidewalls of the channel configured to slidably retain the clip tray and the plurality of surgical clips therein. A reposable surgical clip applier is also provided.

8 Claims, 23 Drawing Sheets

(51) Int. Cl.
*A61B 17/29* (2006.01)
*A61B 17/00* (2006.01)
*A61B 90/00* (2016.01)

(52) U.S. Cl.
CPC ............... *A61B 2017/0046* (2013.01); *A61B 2017/0053* (2013.01); *A61B 2017/00367* (2013.01); *A61B 2017/00473* (2013.01); *A61B 2017/00477* (2013.01); *A61B 2017/2916* (2013.01); *A61B 2017/2922* (2013.01); *A61B 2090/0803* (2016.02)

(56) References Cited

U.S. PATENT DOCUMENTS

| | | |
|---|---|---|
| 3,603,109 A | 9/1971 | Virtanen et al. |
| 3,638,847 A | 2/1972 | Noiles et al. |
| 3,652,151 A | 3/1972 | Kawabe et al. |
| 3,675,688 A | 7/1972 | Bryan et al. |
| 3,735,762 A | 5/1973 | Bryan et al. |
| 3,867,944 A | 2/1975 | Samuels |
| 4,226,242 A | 10/1980 | Jarvik |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Fransue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,259,366 A | 11/1993 | Reydel et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |

(56) References Cited

U.S. PATENT DOCUMENTS

| | | |
|---|---|---|
| 5,354,306 A | 10/1994 | Garvey, III et al. |
| 5,356,064 A | 10/1994 | Green et al. |
| 5,359,993 A | 11/1994 | Slater et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,582,616 A | 12/1996 | Bolduc et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A * | 6/1998 | Cuny .................. A61B 17/1285 227/901 |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,044,971 A | 4/2000 | Esposito et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |

(56) References Cited

U.S. PATENT DOCUMENTS

| | | |
|---|---|---|
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Safer |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,052,504 B2 | 5/2006 | Hughett |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,693 B2 | 1/2008 | Viola |
| 7,316,696 B2 | 1/2008 | Wilson, Jr. et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,510,562 B2 | 3/2009 | Lindsay |
| 7,552,853 B2 | 6/2009 | Mas et al. |
| 7,585,304 B2 | 9/2009 | Hughett |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,248 B2 | 6/2010 | Smith et al. |
| 7,731,724 B2 | 6/2010 | Huitema et al. |
| 7,740,641 B2 | 6/2010 | Huitema |
| 7,752,853 B2 | 7/2010 | Singh et al. |
| 7,753,250 B2 | 7/2010 | Clauson et al. |
| 7,766,207 B2 | 8/2010 | Mather et al. |
| 7,819,886 B2 | 10/2010 | Whitfield et al. |
| 7,887,553 B2 | 2/2011 | Lehman et al. |
| 7,905,890 B2 | 3/2011 | Whitfield et al. |
| 7,942,885 B2 | 5/2011 | Sixto, Jr. et al. |
| 7,963,433 B2 | 6/2011 | Whitman et al. |

(56) References Cited

U.S. PATENT DOCUMENTS

| | | | |
|---|---|---|---|
| 7,988,027 | B2 | 8/2011 | Olson et al. |
| 3,021,378 | A1 | 9/2011 | Sixto, Jr. et al. |
| 8,011,550 | B2 | 9/2011 | Aranyi et al. |
| 8,011,555 | B2 | 9/2011 | Tarinelli et al. |
| 8,016,178 | B2 | 9/2011 | Olson et al. |
| 8,021,375 | B2 | 9/2011 | Aldrich et al. |
| 8,038,686 | B2 | 10/2011 | Huitema et al. |
| 8,048,088 | B2 | 11/2011 | Green et al. |
| 8,056,565 | B2 | 11/2011 | Zergiebel |
| 8,062,310 | B2 | 11/2011 | Shibata et al. |
| 8,066,720 | B2 | 11/2011 | Knodel et al. |
| 8,066,721 | B2 | 11/2011 | Kortenbach et al. |
| 8,066,722 | B2 | 11/2011 | Miyagi et al. |
| 8,070,760 | B2 | 12/2011 | Fujita |
| 8,075,571 | B2 | 12/2011 | Vitali et al. |
| 8,080,021 | B2 | 12/2011 | Griego |
| 8,083,668 | B2 | 12/2011 | Durgin et al. |
| 8,088,061 | B2 | 1/2012 | Wells et al. |
| 8,091,755 | B2 | 1/2012 | Kayan et al. |
| 8,100,926 | B1 | 1/2012 | Filshie et al. |
| 8,128,643 | B2 | 3/2012 | Aranyi et al. |
| 8,133,240 | B2 | 3/2012 | Damarati |
| 8,142,451 | B2 | 3/2012 | Boulnois et al. |
| 8,157,145 | B2 | 4/2012 | Shelton, IV et al. |
| 8,157,149 | B2 | 4/2012 | Olson et al. |
| 8,157,151 | B2 | 4/2012 | Ingmanson et al. |
| 8,172,859 | B2 | 5/2012 | Matsuno et al. |
| 8,172,870 | B2 | 5/2012 | Shipp |
| 8,187,290 | B2 | 5/2012 | Buckman et al. |
| 8,211,120 | B2 | 7/2012 | Itoh |
| 8,211,124 | B2 | 7/2012 | Ainsworth et al. |
| 8,216,255 | B2 | 7/2012 | Smith et al. |
| 8,216,257 | B2 | 7/2012 | Huitema et al. |
| 8,236,012 | B2 | 8/2012 | Molitor et al. |
| 8,246,634 | B2 | 8/2012 | Huitema et al. |
| 8,246,635 | B2 | 8/2012 | Huitema |
| 8,262,678 | B2 | 9/2012 | Matsuoka et al. |
| 8,262,679 | B2 | 9/2012 | Nguyen |
| 8,267,944 | B2 | 9/2012 | Sorrentino et al. |
| 8,267,945 | B2 | 9/2012 | Nguyen et al. |
| 8,267,946 | B2 | 9/2012 | Whitfield et al. |
| 8,272,554 | B2 | 9/2012 | Whitman et al. |
| 8,282,655 | B2 | 10/2012 | Whitfield et al. |
| 8,308,743 | B2 | 11/2012 | Matsuno et al. |
| 8,328,822 | B2 | 12/2012 | Huitema et al. |
| 8,336,556 | B2 | 12/2012 | Zergiebel |
| 8,348,130 | B2 | 1/2013 | Shah et al. |
| 8,357,171 | B2 | 1/2013 | Whitfield et al. |
| 8,366,709 | B2 | 2/2013 | Schechter et al. |
| 8,366,726 | B2 | 2/2013 | Dennis |
| 8,371,491 | B2 | 2/2013 | Huitema et al. |
| 8,372,095 | B2 | 2/2013 | Viola |
| 8,382,773 | B2 | 2/2013 | Whitfield et al. |
| 8,398,655 | B2 | 3/2013 | Cheng et al. |
| 8,403,138 | B2 | 3/2013 | Weisshaupt et al. |
| 8,403,945 | B2 | 3/2013 | Whitfield et al. |
| 8,403,946 | B2 | 3/2013 | Whitfield et al. |
| 8,408,442 | B2 | 4/2013 | Racenet et al. |
| 8,409,222 | B2 | 4/2013 | Whitfield et al. |
| 8,409,223 | B2 | 4/2013 | Sorrentino et al. |
| 8,419,752 | B2 | 4/2013 | Sorrentino et al. |
| 8,430,892 | B2 | 4/2013 | Bindra et al. |
| 8,444,660 | B2 | 5/2013 | Adams et al. |
| 8,465,460 | B2 | 6/2013 | Yodat et al. |
| 8,465,502 | B2 | 6/2013 | Zergiebel |
| 8,475,473 | B2 | 7/2013 | Vandenbroek et al. |
| 8,480,688 | B2 | 7/2013 | Boulnois et al. |
| 8,486,091 | B2 | 7/2013 | Sorrentino et al. |
| 8,491,608 | B2 | 7/2013 | Sorrentino et al. |
| 8,496,673 | B2 | 7/2013 | Nguyen et al. |
| 8,506,580 | B2 | 8/2013 | Zergiebel et al. |
| 8,512,357 | B2 | 8/2013 | Viola |
| 8,518,055 | B1 | 8/2013 | Cardinale et al. |
| 8,523,882 | B2 | 9/2013 | Huitema et al. |
| 8,529,585 | B2 | 9/2013 | Jacobs et al. |
| 8,529,586 | B2 | 9/2013 | Rosenberg et al. |
| 8,529,588 | B2 | 9/2013 | Ahlberg et al. |
| 8,545,486 | B2 | 10/2013 | Malkowski |
| 8,556,920 | B2 | 10/2013 | Huitema et al. |
| 8,568,430 | B2 | 10/2013 | Shipp |
| 8,579,918 | B2 | 11/2013 | Whitfield et al. |
| 8,585,717 | B2 | 11/2013 | Sorrentino et al. |
| 8,652,152 | B2 | 2/2014 | Aranyi et al. |
| 8,663,247 | B2 | 3/2014 | Menn et al. |
| 8,685,048 | B2 | 4/2014 | Adams et al. |
| 8,690,899 | B2 | 4/2014 | Kogiso et al. |
| 8,708,213 | B2 | 4/2014 | Shelton, IV et al. |
| 8,709,027 | B2 | 4/2014 | Adams et al. |
| 8,715,299 | B2 | 5/2014 | Menn et al. |
| 8,720,766 | B2 | 5/2014 | Hess et al. |
| 8,734,469 | B2 | 5/2014 | Pribanic et al. |
| 8,747,423 | B2 | 6/2014 | Whitfield et al. |
| 8,753,356 | B2 | 6/2014 | Vitali et al. |
| 8,814,884 | B2 | 8/2014 | Whitfield et al. |
| 8,821,516 | B2 | 9/2014 | Huitema |
| 8,839,954 | B2 | 9/2014 | Disch |
| 8,845,659 | B2 | 9/2014 | Whitfield et al. |
| 8,894,665 | B2 | 11/2014 | Sorrentino et al. |
| 8,894,666 | B2 | 11/2014 | Schulz et al. |
| 8,900,253 | B2 | 12/2014 | Aranyi et al. |
| 8,915,930 | B2 | 12/2014 | Huitema et al. |
| 8,920,438 | B2 | 12/2014 | Aranyi et al. |
| 8,939,974 | B2 | 1/2015 | Boudreaux et al. |
| 8,950,646 | B2 | 2/2015 | Viola |
| 8,961,542 | B2 | 2/2015 | Whitfield et al. |
| 8,968,337 | B2 | 3/2015 | Whitfield et al. |
| 8,968,342 | B2 | 3/2015 | Wingardner, III et al. |
| 8,973,804 | B2 | 3/2015 | Hess et al. |
| 9,011,464 | B2 | 4/2015 | Zammataro |
| 9,011,465 | B2 | 4/2015 | Whitfield et al. |
| 9,089,334 | B2 | 7/2015 | Sorrentino et al. |
| 9,113,892 | B2 | 8/2015 | Malkowski et al. |
| 9,113,893 | B2 | 8/2015 | Sorrentino et al. |
| 9,119,629 | B2 | 9/2015 | Cardinale et al. |
| 9,186,136 | B2 | 11/2015 | Malkowski et al. |
| 9,186,153 | B2 | 11/2015 | Zammataro |
| 9,208,429 | B2 | 12/2015 | Thornton et al. |
| 9,220,507 | B1 | 12/2015 | Patel et al. |
| 9,282,972 | B1 | 3/2016 | Patel et al. |
| 9,326,776 | B2 | 5/2016 | Gadberry et al. |
| 9,358,011 | B2 | 6/2016 | Sorrentino et al. |
| 9,364,216 | B2 | 6/2016 | Rockrohr et al. |
| 9,364,240 | B2 | 6/2016 | Whitfield et al. |
| 9,370,400 | B2 | 6/2016 | Parihar |
| 9,393,024 | B2 | 7/2016 | Whitfield et al. |
| 9,408,610 | B2 | 8/2016 | Hartoumbekis |
| 9,414,844 | B2 | 8/2016 | Zergiebel et al. |
| 9,433,411 | B2 | 9/2016 | Racenet et al. |
| 9,445,810 | B2 | 9/2016 | Cappola |
| 9,498,227 | B2 | 11/2016 | Zergiebel et al. |
| 9,526,501 | B2 | 12/2016 | Malkowski |
| 9,526,565 | B2 | 12/2016 | Strobl |
| 9,545,254 | B2 | 1/2017 | Sorrentino et al. |
| 9,561,038 | B2 | 2/2017 | Shelton, IV et al. |
| 9,642,627 | B2 | 5/2017 | Zammataro |
| 9,687,247 | B2 | 6/2017 | Aranyi et al. |
| 9,717,504 | B2 | 8/2017 | Huitema |
| 9,717,505 | B2 | 8/2017 | Whitfield et al. |
| 9,737,310 | B2 | 8/2017 | Whitfield et al. |
| 9,750,500 | B2 | 9/2017 | Malkowski |
| 9,763,668 | B2 | 9/2017 | Whitfield et al. |
| 9,775,623 | B2 | 10/2017 | Zammataro et al. |
| 9,775,624 | B2 | 10/2017 | Rockrohr et al. |
| 9,782,181 | B2 | 10/2017 | Vitali et al. |
| 9,848,886 | B2 | 12/2017 | Malkowski et al. |
| 9,855,043 | B2 | 1/2018 | Malkowski |
| 9,931,124 | B2 | 4/2018 | Gokharu |
| 9,968,361 | B2 | 5/2018 | Aranyi et al. |
| 9,968,362 | B2 | 5/2018 | Malkowski et al. |
| 10,004,502 | B2 | 6/2018 | Malkowski et al. |
| 10,136,939 | B2 | 11/2018 | Minnelli et al. |
| 10,159,484 | B2 | 12/2018 | Sorrentino et al. |
| 10,159,491 | B2 | 12/2018 | Gokharu |
| 10,159,492 | B2 | 12/2018 | Zammataro |

(56) References Cited

U.S. PATENT DOCUMENTS

| | | |
|---|---|---|
| 10,166,027 B2 | 1/2019 | Aranyi et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,271,854 B2 | 4/2019 | Whitfield et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 10,470,765 B2 | 11/2019 | Malkowski |
| 10,485,538 B2 | 11/2019 | Whitfield et al. |
| 10,492,795 B2 | 12/2019 | Williams |
| 10,537,329 B2 | 1/2020 | Malkowski |
| 10,542,999 B2 | 1/2020 | Zergiebel |
| 10,548,602 B2 | 2/2020 | Baril et al. |
| 10,568,635 B2 | 2/2020 | Whitfield et al. |
| 10,582,931 B2 | 3/2020 | Mujawar |
| 10,603,038 B2 | 3/2020 | Mujawar et al. |
| 10,610,236 B2 | 4/2020 | Baril |
| 10,639,032 B2 | 5/2020 | Baril et al. |
| 10,639,044 B2 | 5/2020 | Prior |
| 10,653,429 B2 | 5/2020 | Baril et al. |
| 10,660,639 B2 | 5/2020 | Hartoumbekis |
| 10,660,651 B2 | 5/2020 | Baril et al. |
| 10,660,652 B2 | 5/2020 | Tan et al. |
| 10,660,723 B2 | 5/2020 | Baril |
| 10,660,725 B2 | 5/2020 | Baril et al. |
| 10,675,043 B2 | 6/2020 | P V R |
| 10,675,112 B2 | 6/2020 | Baril et al. |
| 10,682,135 B2 | 6/2020 | Sorrentino et al. |
| 10,682,146 B2 | 6/2020 | Rockrohr et al. |
| 10,702,278 B2 | 7/2020 | Tokarz et al. |
| 10,702,279 B2 | 7/2020 | Xu et al. |
| 10,702,280 B2 | 7/2020 | Cai et al. |
| 10,709,455 B2 | 7/2020 | Baril et al. |
| 10,722,235 B2 | 7/2020 | Baril et al. |
| 10,722,236 B2 | 7/2020 | Zammataro |
| 10,743,851 B2 | 8/2020 | Swayze et al. |
| 10,743,886 B2 | 8/2020 | Malkowski et al. |
| 10,743,887 B2 | 8/2020 | P V R |
| 10,758,234 B2 | 9/2020 | Malkowski et al. |
| 10,758,244 B2 | 9/2020 | Williams |
| 10,758,245 B2 | 9/2020 | Baril et al. |
| 10,765,431 B2 | 9/2020 | Hu et al. |
| 10,765,435 B2 | 9/2020 | Gokharu |
| 10,786,262 B2 | 9/2020 | Baril et al. |
| 10,786,263 B2 | 9/2020 | Baril et al. |
| 10,786,273 B2 | 9/2020 | Baril et al. |
| 10,806,463 B2 | 10/2020 | Hartoumbekis |
| 10,806,464 B2 | 10/2020 | Raikar et al. |
| 10,828,036 B2 | 11/2020 | Baril et al. |
| 10,828,044 B2 | 11/2020 | Gokharu |
| 10,835,260 B2 | 11/2020 | Baril et al. |
| 10,835,341 B2 | 11/2020 | Baril et al. |
| 10,849,630 B2 | 12/2020 | P V R |
| 10,863,992 B2 | 12/2020 | Czernik et al. |
| 10,932,791 B2 | 3/2021 | P V R |
| 10,932,793 B2 | 3/2021 | Yi et al. |
| 10,945,734 B2 | 3/2021 | Baril et al. |
| 10,959,737 B2 | 3/2021 | P V R |
| 10,993,721 B2 | 5/2021 | Baril et al. |
| 11,026,696 B2 | 6/2021 | Zammataro |
| 11,033,256 B2 | 6/2021 | Zammataro et al. |
| 11,051,827 B2 | 7/2021 | Baril et al. |
| 11,051,828 B2 | 7/2021 | Baril et al. |
| 11,058,432 B2 | 7/2021 | Bhatnagar et al. |
| 11,071,553 B2 | 7/2021 | Raikar et al. |
| 11,116,513 B2 | 9/2021 | Dinino et al. |
| 11,116,514 B2 | 9/2021 | Yue et al. |
| 11,134,956 B2 | 10/2021 | Shankarsetty |
| 11,147,566 B2 | 10/2021 | Pilletere et al. |
| 11,213,298 B2 | 1/2022 | Sorrentino et al. |
| 11,213,299 B2 | 1/2022 | Whitfield et al. |
| 2001/0047178 A1 | 11/2001 | Peters |
| 2002/0040226 A1 | 4/2002 | Laufer et al. |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0123742 A1 | 9/2002 | Baxter et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto et al. |
| 2002/0198540 A1 | 12/2002 | Smith et al. |
| 2002/0198541 A1 | 12/2002 | Smith et al. |
| 2003/0014060 A1 | 1/2003 | Wilson et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake |
| 2003/0167063 A1 | 9/2003 | Kerr |
| 2003/0208231 A1 | 11/2003 | Williamson et al. |
| 2003/0220657 A1 | 11/2003 | Adams |
| 2003/0225423 A1 | 12/2003 | Huitema |
| 2003/0229360 A1 | 12/2003 | Gayton |
| 2003/0233105 A1 | 12/2003 | Gayton |
| 2004/0010272 A1 | 1/2004 | Manetakis et al. |
| 2004/0044352 A1 | 3/2004 | Fowler et al. |
| 2004/0097970 A1 | 5/2004 | Hughett |
| 2004/0097971 A1 | 5/2004 | Hughett |
| 2004/0097972 A1 | 5/2004 | Shipp et al. |
| 2004/0106936 A1 | 6/2004 | Shipp et al. |
| 2004/0133215 A1 | 7/2004 | Baxter |
| 2004/0138681 A1 | 7/2004 | Pier |
| 2004/0153100 A1 | 8/2004 | Ahlberg et al. |
| 2004/0158266 A1 | 8/2004 | Damarati |
| 2004/0162567 A9 | 8/2004 | Adams |
| 2004/0167545 A1 | 8/2004 | Sadler et al. |
| 2004/0176776 A1 | 9/2004 | Zubok et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0230198 A1 | 11/2004 | Manzi et al. |
| 2004/0232197 A1 | 11/2004 | Shelton et al. |
| 2005/0010242 A1 | 1/2005 | Lindsay |
| 2005/0080440 A1 | 4/2005 | Durgin et al. |
| 2005/0085830 A1 | 4/2005 | Lehman et al. |
| 2005/0090837 A1 | 4/2005 | Sixto et al. |
| 2005/0090838 A1 | 4/2005 | Sixto et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0175703 A1 | 8/2005 | Hunter et al. |

(56) References Cited

U.S. PATENT DOCUMENTS

| | | |
|---|---|---|
| 2005/0177176 A1 | 8/2005 | Gerbi et al. |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0000867 A1 | 1/2006 | Shelton et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079115 A1 | 4/2006 | Aranyi |
| 2006/0079913 A1* | 4/2006 | Whitfield ........... A61B 17/0682 606/142 |
| 2006/0085015 A1 | 4/2006 | Whitfield et al. |
| 2006/0085021 A1 | 4/2006 | Wenzler |
| 2006/0100649 A1 | 5/2006 | Hart |
| 2006/0111731 A1 | 5/2006 | Manzo |
| 2006/0124485 A1 | 6/2006 | Kennedy |
| 2006/0129170 A1 | 6/2006 | Royce et al. |
| 2006/0135992 A1 | 6/2006 | Bettuchi et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0212050 A1 | 9/2006 | D'Agostino et al. |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0241655 A1 | 10/2006 | Viola |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0021766 A1 | 1/2007 | Belagali et al. |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | de la Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0066981 A1 | 3/2007 | Meagher |
| 2007/0073314 A1 | 3/2007 | Gadberry et al. |
| 2007/0083218 A1 | 4/2007 | Morris |
| 2007/0093790 A1 | 4/2007 | Downey et al. |
| 2007/0093856 A1 | 4/2007 | Whitfield et al. |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto et al. |
| 2007/0149988 A1 | 6/2007 | Michler et al. |
| 2007/0149989 A1 | 6/2007 | Santilli et al. |
| 2007/0162060 A1 | 7/2007 | Wild |
| 2007/0173866 A1 | 7/2007 | Sorrentino et al. |
| 2007/0175949 A1 | 8/2007 | Shelton et al. |
| 2007/0185504 A1 | 8/2007 | Manetakis et al. |
| 2007/0191868 A1 | 8/2007 | Theroux et al. |
| 2007/0203509 A1 | 8/2007 | Bettuchi |
| 2007/0203510 A1 | 8/2007 | Bettuchi |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0083813 A1 | 4/2008 | Zemlok et al. |
| 2008/0103510 A1 | 5/2008 | Taylor et al. |
| 2008/0147092 A1 | 6/2008 | Rogge et al. |
| 2008/0147093 A1 | 6/2008 | Roskopf et al. |
| 2008/0154287 A1 | 6/2008 | Rosenberg et al. |
| 2008/0167665 A1 | 7/2008 | Arp et al. |
| 2008/0167671 A1 | 7/2008 | Giordano et al. |
| 2008/0228199 A1 | 9/2008 | Cropper et al. |
| 2008/0243145 A1 | 10/2008 | Whitfield et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312665 A1 | 12/2008 | Shibata et al. |
| 2008/0312670 A1 | 12/2008 | Lutze et al. |
| 2008/0319456 A1 | 12/2008 | Hart |
| 2009/0076533 A1 | 3/2009 | Kayan et al. |
| 2009/0088777 A1 | 4/2009 | Miyagi et al. |
| 2009/0088783 A1 | 4/2009 | Kennedy et al. |
| 2009/0171380 A1 | 7/2009 | Whiting |
| 2009/0182193 A1 | 7/2009 | Whitman et al. |
| 2009/0204115 A1 | 8/2009 | Dees, Jr. et al. |
| 2009/0209946 A1 | 8/2009 | Swayze et al. |
| 2009/0222003 A1 | 9/2009 | Otley |
| 2009/0228023 A1 | 9/2009 | Cui |
| 2009/0228024 A1 | 9/2009 | Whitfield et al. |
| 2009/0261142 A1 | 10/2009 | Milliman et al. |
| 2009/0264904 A1 | 10/2009 | Mdrich et al. |
| 2009/0299382 A1 | 12/2009 | Zergiebel |
| 2009/0312775 A1 | 12/2009 | Gilkey et al. |
| 2009/0326558 A1 | 12/2009 | Cui et al. |

(56) References Cited

U.S. PATENT DOCUMENTS

| | | |
|---|---|---|
| 2010/0049216 A1 | 2/2010 | Zergiebel |
| 2010/0057102 A1 | 3/2010 | Sorrentino et al. |
| 2010/0057105 A1 | 3/2010 | Sorrentino |
| 2010/0069935 A1 | 3/2010 | Crainich |
| 2010/0089970 A1 | 4/2010 | Smith et al. |
| 2010/0274262 A1 | 10/2010 | Schulz et al. |
| 2010/0274264 A1 | 10/2010 | Schulz et al. |
| 2010/0318103 A1 | 12/2010 | Cheng et al. |
| 2010/0331862 A1 | 12/2010 | Monassevitch et al. |
| 2011/0028994 A1 | 2/2011 | Whitfield et al. |
| 2011/0054498 A1 | 3/2011 | Monassevitch et al. |
| 2011/0082474 A1 | 4/2011 | Bindra et al. |
| 2011/0087220 A1 | 4/2011 | Felder et al. |
| 2011/0087241 A1 | 4/2011 | Nguyen |
| 2011/0087243 A1* | 4/2011 | Nguyen ............ A61B 17/1285 606/143 |
| 2011/0087268 A1 | 4/2011 | Livneh |
| 2011/0101066 A1 | 5/2011 | Farascioni et al. |
| 2011/0112552 A1 | 5/2011 | Lehman et al. |
| 2011/0137323 A1 | 6/2011 | Malkowski et al. |
| 2011/0137324 A1 | 6/2011 | Boudreaux et al. |
| 2011/0144662 A1 | 6/2011 | McLawhorn et al. |
| 2011/0144665 A1 | 6/2011 | Malkowski |
| 2011/0190791 A1 | 8/2011 | Jacobs et al. |
| 2011/0208211 A1 | 8/2011 | Whitfield et al. |
| 2011/0208212 A1 | 8/2011 | Zergiebel et al. |
| 2011/0218553 A1 | 9/2011 | Huitema et al. |
| 2011/0218554 A1 | 9/2011 | Cheng et al. |
| 2011/0218555 A1 | 9/2011 | Huitema |
| 2011/0218556 A1 | 9/2011 | Nguyen et al. |
| 2011/0224696 A1 | 9/2011 | Huitema et al. |
| 2011/0224700 A1 | 9/2011 | Schmidt et al. |
| 2011/0224701 A1 | 9/2011 | Menn |
| 2011/0230900 A1 | 9/2011 | Sarradon |
| 2011/0245847 A1 | 10/2011 | Menn et al. |
| 2011/0245848 A1 | 10/2011 | Rosenberg et al. |
| 2011/0251608 A1 | 10/2011 | Timm et al. |
| 2011/0295290 A1 | 12/2011 | Whitfield |
| 2011/0313437 A1 | 12/2011 | Yeh |
| 2012/0022526 A1 | 1/2012 | Aldridge et al. |
| 2012/0029533 A1* | 2/2012 | Whitfield ............ A61B 17/10 606/143 |
| 2012/0029534 A1 | 2/2012 | Whitfield |
| 2012/0041455 A1 | 2/2012 | Martinez |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0059394 A1 | 3/2012 | Brenner et al. |
| 2012/0065647 A1 | 3/2012 | Litscher et al. |
| 2012/0109158 A1 | 5/2012 | Zammataro |
| 2012/0116420 A1 | 5/2012 | Sorrentino et al. |
| 2012/0197269 A1 | 8/2012 | Zammataro |
| 2012/0226291 A1 | 9/2012 | Malizia et al. |
| 2012/0234894 A1 | 9/2012 | Kostrzewski |
| 2012/0253298 A1 | 10/2012 | Henderson et al. |
| 2012/0265220 A1 | 10/2012 | Menn |
| 2012/0277765 A1 | 11/2012 | Zammataro et al. |
| 2012/0330326 A1 | 12/2012 | Creston et al. |
| 2013/0041379 A1 | 2/2013 | Bodor et al. |
| 2013/0110135 A1 | 5/2013 | Whitfield et al. |
| 2013/0131697 A1 | 5/2013 | Hartoumbekis |
| 2013/0165951 A1 | 6/2013 | Blake, III |
| 2013/0165952 A1 | 6/2013 | Whitfield et al. |
| 2013/0172909 A1 | 7/2013 | Harris |
| 2013/0172910 A1 | 7/2013 | Malkowski |
| 2013/0172912 A1 | 7/2013 | Whitfield et al. |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2013/0274767 A1 | 10/2013 | Sorrentino et al. |
| 2013/0289583 A1 | 10/2013 | Zergiebel et al. |
| 2013/0296892 A1 | 11/2013 | Sorrentino et al. |
| 2013/0325057 A1 | 12/2013 | Larson et al. |
| 2014/0005678 A1 | 1/2014 | Shelton, IV et al. |
| 2014/0005693 A1 | 1/2014 | Shelton, IV et al. |
| 2014/0058412 A1 | 2/2014 | Aranyi et al. |
| 2014/0074143 A1 | 3/2014 | Fitzgerald et al. |
| 2014/0131421 A1 | 5/2014 | Viola |
| 2014/0188159 A1 | 7/2014 | Steege |
| 2014/0194903 A1 | 7/2014 | Malkowski et al. |
| 2014/0207156 A1 | 7/2014 | Malkowski |
| 2014/0252065 A1 | 9/2014 | Hessler et al. |
| 2014/0263565 A1 | 9/2014 | Lytle, IV et al. |
| 2014/0276970 A1 | 9/2014 | Messerly et al. |
| 2014/0296879 A1 | 10/2014 | Menn et al. |
| 2014/0309677 A1 | 10/2014 | Baldwin |
| 2014/0324074 A1 | 10/2014 | Crainich et al. |
| 2014/0371728 A1 | 12/2014 | Vaughn |
| 2014/0379003 A1* | 12/2014 | Blake, III ............ A61B 17/128 606/143 |
| 2015/0032131 A1 | 1/2015 | Sorrentino et al. |
| 2015/0045816 A1 | 2/2015 | Aranyi et al. |
| 2015/0066057 A1 | 3/2015 | Rockrohr et al. |
| 2015/0080916 A1 | 3/2015 | Aranyi et al. |
| 2015/0127022 A1 | 5/2015 | Whitfield et al. |
| 2015/0164511 A1 | 6/2015 | Whitfield et al. |
| 2015/0190133 A1 | 7/2015 | Penna et al. |
| 2015/0190138 A1 | 7/2015 | Whitfield et al. |
| 2015/0190139 A1 | 7/2015 | Zammataro |
| 2015/0196298 A1 | 7/2015 | Menn et al. |
| 2015/0201953 A1 | 7/2015 | Strobl et al. |
| 2015/0265282 A1 | 9/2015 | Miles et al. |
| 2015/0313452 A1 | 11/2015 | Hasser et al. |
| 2015/0314451 A1 | 11/2015 | Nixon |
| 2015/0327879 A1 | 11/2015 | Garrison et al. |
| 2015/0351771 A1 | 12/2015 | Malkowski et al. |
| 2015/0351772 A1 | 12/2015 | Malkowski et al. |
| 2016/0000428 A1 | 1/2016 | Scirica |
| 2016/0004956 A1 | 1/2016 | Reynolds et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0166255 A1 | 6/2016 | Fischvogt |
| 2016/0192927 A1 | 7/2016 | Kostrzewski |
| 2016/0213377 A1 | 7/2016 | Shankarsetty |
| 2016/0242767 A1 | 8/2016 | Kasvikis |
| 2016/0249927 A1 | 9/2016 | Beckman et al. |
| 2016/0262764 A1 | 9/2016 | Gokharu |
| 2016/0296232 A1 | 10/2016 | Campbell |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0165015 A1 | 6/2017 | Hess et al. |
| 2017/0172780 A1 | 6/2017 | Murthy Aravalli |
| 2017/0202567 A1 | 7/2017 | Griffiths et al. |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0258472 A1 | 9/2017 | Aranyi et al. |
| 2017/0290587 A1 | 10/2017 | Schober et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0021041 A1 | 1/2018 | Zhang et al. |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |

(56) References Cited

U.S. PATENT DOCUMENTS

| | | |
|---|---|---|
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czemik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133590 A1 | 5/2019 | Richard |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0159782 A1 | 5/2019 | Kamaraj et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |
| 2019/0298377 A1 | 10/2019 | Castro |
| 2019/0321048 A1 | 10/2019 | Dinino et al. |
| 2019/0328391 A1 | 10/2019 | Holsten et al. |
| 2019/0328399 A1 | 10/2019 | Baril et al. |
| 2020/0008806 A1 | 1/2020 | Dinino et al. |
| 2020/0046329 A1 | 2/2020 | Baril et al. |
| 2020/0046359 A1 | 2/2020 | Thomas et al. |
| 2020/0046363 A1 | 2/2020 | Baril et al. |
| 2020/0046365 A1 | 2/2020 | Baril et al. |
| 2020/0046443 A1 | 2/2020 | Baril et al. |
| 2020/0060686 A1 | 2/2020 | Williams |
| 2020/0113569 A1 | 4/2020 | Zergiebel |
| 2020/0129183 A1 | 4/2020 | Baril et al. |
| 2020/0146687 A1 | 5/2020 | Whitfield et al. |
| 2020/0170646 A1 | 6/2020 | Mujawar |
| 2020/0229825 A1 | 7/2020 | P V R |
| 2020/0261095 A1 | 8/2020 | Yi et al. |
| 2020/0315629 A1 | 10/2020 | Xu et al. |
| 2021/0059681 A1 | 3/2021 | Zhang et al. |
| 2021/0169482 A1 | 6/2021 | Baril et al. |
| 2021/0204946 A1 | 7/2021 | Banerjee et al. |
| 2021/0298758 A1 | 9/2021 | Thomas et al. |
| 2021/0401438 A1 | 12/2021 | Pilletere et al. |

FOREIGN PATENT DOCUMENTS

| | | |
|---|---|---|
| CN | 1 939 231 A | 4/2007 |
| CN | 101164502 A | 4/2008 |
| CN | 202699217 U | 1/2013 |
| CN | 103251441 A | 8/2013 |
| CN | 104605911 B | 2/2017 |
| DE | 29520789 U1 | 6/1996 |
| DE | 20 2005 001664 U1 | 5/2005 |
| DE | 202007003398 U1 | 6/2007 |
| DE | 202009006113 U1 | 7/2009 |
| EP | 0000756 A1 | 2/1979 |
| EP | 0406724 A1 | 1/1991 |
| EP | 0409569 A1 | 1/1991 |
| EP | 0514139 A2 | 11/1992 |
| EP | 0576835 A2 | 1/1994 |
| EP | 0732078 A2 | 9/1996 |
| EP | 2421446 A1 | 2/2012 |
| EP | 2609877 A1 | 7/2013 |
| EP | 3132756 A1 | 2/2017 |
| EP | 3476331 A1 | 5/2019 |
| GB | 2073022 A | 10/1981 |
| JP | 06054858 | 3/1994 |
| JP | 2003033361 A | 2/2003 |
| JP | 2006154230 A | 6/2006 |
| JP | 2006277221 A | 10/2006 |
| JP | 2008017876 A | 1/2008 |
| JP | 2008200190 A | 9/2008 |
| JP | 2011186812 A | 9/2011 |
| JP | 2013166982 A | 8/2013 |
| WO | 9003763 A1 | 4/1990 |
| WO | 9624294 A1 | 8/1996 |
| WO | 0042922 A1 | 7/2000 |
| WO | 0166001 A2 | 9/2001 |
| WO | 0167965 A1 | 9/2001 |
| WO | 03005911 A1 | 1/2003 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |
| WO | 2017084000 A1 | 5/2017 |
| WO | 2017146138 A1 | 8/2017 |
| WO | 2018035796 A1 | 3/2018 |

OTHER PUBLICATIONS

Canadian Office Action corresponding to counterpart Int'l Application No. CA 2,676,547 dated Nov. 25, 2015.
Extended European Search Report corresponding to counterpart Int'l Application No. EP 15 17 3809.3 dated Nov. 25, 2015.
Chinese Office Action corresponding to counterpart Int'l Application No. CN 201210586814.9 dated Dec. 2, 2015.
Extended European Search Report corresponding to counterpart Int'l Application No. EP 12 17 2940.4 dated Dec. 14, 2015.
Chinese First Office Action corresponding to counterpart Int'l Appln. No. CN 201210586826.1 dated Dec. 30, 2015.
Extended European Search Report corresponding to counterpart Int'l Appln. No. EP 15 18 5362.9 dated Feb. 12, 2016.
Extended European Search Report corresponding to counterpart Int'l Appln. No. EP 12 19 7813.4 dated Mar. 7, 2016.
Canadian Office Action corresponding to counterpart Int'l Appln. No. CA 2,676,465 dated Mar. 8, 2016.
Japanese Office Action corresponding to counterpart Int'l Appln. No. JP 2014-245081, dated Mar. 18, 2016.
Japanese Office Action corresponding to counterpart Int'l Appln. No. JP 2015-005629 dated Mar. 18, 2016.
Extended European Search Report corresponding to counterpart Int'l Appln. No. EP 15 19 3549.1 dated Mar. 22, 2016.
International Search Report and Written Opinion corresponding to counterpart Int'l Appln. No. PCT/CN2015/082199 dated Mar. 31, 2016.
Extended European Search Report corresponding to counterpart Int'l Appln. No. EP 15 19 7251.0 dated Apr. 8, 2016.
Extended European Search Report corresponding to counterpart Int'l Appln. No. EP 16 15 0739.7 dated May 17, 2016.
Canadian Office Action corresponding to counterpart Int'l Appln. No. CA 2,716,672 dated May 31, 2016.
Canadian Office Action corresponding to counterpart Int'l Appln. No. CA 2,717,448 dated May 31, 2016.
Canadian Office Action corresponding to counterpart Int'l Appln. No. CA 2,721,951, dated Jun. 1, 2016.
Partial European Search Report corresponding to counterpart Int'l Appln. No. EP 16 15 0287.7 dated Jun. 16, 2016.
Chinese Second Office Action corresponding to counterpart Int'l Appln. No. CN 201210555570.8 dated Jun. 20, 2016.

(56) References Cited

OTHER PUBLICATIONS

International Search Report corresponding to Int'l Patent Appln. PCT/US2018/050316 dated Dec. 31, 2018.
International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2019.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.
Extended European Search Report corresponding to European Patent Application EP 15905685.2 dated May 29, 2019.
European Office Action corresponding to European Patent Application EP 17157606.9 dated Jul. 2, 2 019.
Extended European Search Report corresponding to European Patent Application EP 15908025.8 dated Jul. 2, 2019.
Extended European Search Report corresponding to European Patent Application EP 18212054.3 dated Jul. 3, 2019.
Partial Supplementary European Search Report corresponding to European Patent Application EP 16884297.9 dated Jul. 30, 2019.
European Examination Report dated Jul. 2, 2019 issued in corresponding EP Appln. No. 17 157 606.9-1122.
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6401.1, completed Nov. 22, 2012 and dated Nov. 30, 2012; (7 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 19 1706.6, completed Dec. 19, 2012 and dated Jan. 8, 2013; (6 Pages).
The Extended European Search Report corresponding to EP 12 19 8745 7, completed Mar. 19, 2013 and dated Apr. 11, 2013; (8 Pages).
The Extended European Search Report corresponding to EP 12 15 2989 5, completed Apr. 9, 2013 and dated Apr. 18, 2013; (9 Pages).
The Extended European Search Report corresponding to EP 08 73 2820 9, completed Jul. 2, 2013 and dated Jul. 9, 2013; (10 Pages).
The Extended European Search Report corresponding to EP 13 17 2008 8, completed Aug. 14, 2013 and dated Aug. 28, 2013; (8 Pages).
The Extended European Search Report corresponding to EP 13 16 6382.5, completed Nov. 19, 2013 and dated Nov. 28, 2013; (8 Pages).
The Extended European Search Report corresponding to EP 11 25 0194.5, completed Nov. 25, 2013 and dated Dec. 3, 2013; (8 Pages).
The Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
The Extended European Search Report corresponding to EP 10 25 2112.7, completed Jul. 29, 2014 and dated Aug. 5, 2014; (8 pp).
The Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.
European Office Action corresponding to European Appln. No. EP 16 15 9324.9 dated Aug. 7, 2017.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.
European Office Action corresponding to EP 12 152 989.5 dated May 4, 2015.
Australian Office Action corresponding to AU 2009212759 dated May 7, 2015.
Chinese Office Action corresponding to counterpart Int'l Appln No. CN 201210212642.9 dated Jun. 3, 2015.
European Office Action corresponding to counterpart Int'l Appln No. EP 04 719 757.9 dated Jun. 12, 2015.
European Office Action corresponding to counterpart Int'l Appln No. EP 13 166 382.5 dated Jun. 19, 2015.
Japanese Office Action corresponding to counterpart Int'l Application No. JP 2010-226908 dated Jun. 26, 2015.
Extended European Search Report corresponding to counterpart Int'l Application No. EP 15 15 5024.1 dated Jul. 17, 2015.
Extended European Search Report corresponding to counterpart Int'l Application No. EP 14 19 2026.4 dated Jul. 17, 2015.
Japanese Office Action corresponding to counterpart Int'l Application No. JP 2011-160126 dated Aug. 10, 2015.
Extended European Search Report corresponding to counterpart Int'l Application No. EP 14 15 0321.9 dated Sep. 23, 2015.
Extended European Search Report corresponding to counterpart Int'l Application No. EP 11 25 0675.3 dated Oct. 7, 2015.
Extended European Search Report corresponding to counterpart Int'l Application No. EP 11 25 0674.6 dated Oct. 7, 2015.
Extended European Search Report corresponding to counterpart Int'l Application No. EP 12 19 3447.5 dated Oct. 19, 2015.
Canadian Office Action corresponding to counterpart Int'l Application No. CA 2,675,875 dated Oct. 26, 2015.

(56) References Cited

OTHER PUBLICATIONS

Japanese Office Action corresponding to counterpart Int'l Application No. JP 2015-005629 dated Oct. 28, 2015.
Japanese Office Action corresponding to counterpart Int'l Application No. JP 2014-245081 dated Oct. 28, 2015.
Canadian Office Action corresponding to counterpart Int'l Application No. CA 2,675,921 dated Oct. 30, 2015.
Chinese Office Action corresponding to counterpart Int'l Application No. CN 201210555570.8 dated Nov. 2, 2015.
Canadian Office Action corresponding to counterpart Int'l Application No. CA 2,676,309 dated Nov. 3, 2015.
Extended European Search Report for Application No. 17157606 dated May 22, 2017.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 3447.5 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
European Office Action corresponding to European Appln. No. EP 11 25 0674.6 dated May 23, 2017.
Canadian Office Action corresponding to Canadian Appln. No. CA 2,743,402 dated May 30, 2017.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2 018.
Extended European Search Report corresponding to Patent Application EP 18157789.1 dated Jul. 5, 2 018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.
The extended European Search Report corresponding to European Application No. EP 07 25 3905.9, completed Jan. 29, 2008; dated Feb. 7, 2008; (7 Pages).
International Search Report corresponding to International Application No. PCT-US08-58185, completed Sep. 4, 2008; dated Sep. 9, 2008; (2 Pages).

The International Search Report corresponding to International Application No. PCT-US08-59859, completed Sep. 14, 2008; dated Sep. 18, 2008; (2 Pages).
The extended European Search Report corresponding to European Application No. EP 07 25 3807.7, completed Nov. 7, 2008; dated Nov. 26, 2008; (11 Pages).
The extended European Search Report corresponding to European Application No. EP 09 25 2049.3, completed Dec. 11, 2009; dated Jan. 12, 2010; (3 Pages).
The extended European Search Report corresponding to European Application No. EP 09 25 2050.1, completed Dec. 23, 2009; dated Jan. 21, 2010; (3 Pages).
The extended European Search Report corresponding to European Application No. EP 09 25 2051.9, completed Dec. 21, 2009; dated Jan. 28, 2010; (3 Pages).
The extended European Search Report corresponding to European Application No. EP 09 25 2052.7, completed Nov. 16, 2009; dated Nov. 24, 2009; (3 Pages).
The extended European Search Report corresponding to European Application No. EP 09 25 2053.5, completed Nov. 24, 2009; dated Dec. 1, 2009; (3 Pages).
The extended European Search Report corresponding to European Application No. EP 09 25 2054.3, completed Jan. 7, 2010; dated Jan. 22, 2010; (3 Pages).
The extended European Search Report corresponding to European Application No. EP 09 25 2056.8, completed Jan. 3, 2010; dated Feb. 5, 2010; (3 Pages).
The extended European Search Report corresponding to European Application No. EP 10 25 0497.4, completed May 1, 2010; dated May 12, 2010; (6 Pages).
The extended European Search Report corresponding to European Application No. EP 10 25 2079.8, completed Mar. 3, 2011; dated Mar. 17, 2011; (3 Pages).
The European Search Report corresponding to European Application No. EP 05 81 0218.7, completed Apr. 18, 2011; dated May 20, 2011; (3 pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 9, 2011; dated May 20, 2011; (4 pages).
The extended European Search Report corresponding to European Application No. EP 11 25 0214.1, completed May 25, 2011; dated Jun. 1, 2011; (3 Pages).
The extended European Search Report corresponding to European Application No. EP 11 00 2681.2, completed May 31, 2011; dated Jun. 10, 2011; (3 Pages).
The European Search Report corresponding to European Application No. EP 05 80 2686.5, completed Jan. 9, 2012; dated Jan. 18, 2012; (3 Pages).
The extended European Search Report corresponding to European Application No. EP 12 15 1313.9, completed Mar. 20, 2012 and dated Apr. 12, 2012; (5 Pages).
The extended European Search Report corresponding to European Application No. EP 12 16 1291.5, completed Apr. 24, 2012 and dated May 4, 2012; (5 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 2288.0, completed Jun. 1, 2012 and dated Jul. 7, 2012; (6 Pages).
The extended European Search Report corresponding to European Application No. EP 12 16 4955.2, completed Aug. 23, 2012 and dated Sep. 4, 2012; (5 Pages).
International Search Report and Written Opinion corresponding to International Application No. PCT/US18/050316 dated Dec. 31, 2018.
International Search Report and Written Opinion corresponding to International Application No. PCT/US18/050325 dated Jan. 7, 2019.

(56) References Cited

OTHER PUBLICATIONS

International Search Report and Written Opinion corresponding to International Application No. PCT/US2018/057922 dated Feb. 22, 2019.
Chinese First Office Action corresponding to Patent Application CN 201610055870.8 dated Aug. 1, 2019.
Japanese Office Action corresponding to Patent Application JP 2015-203499 dated Aug. 16, 2019.
Chinese Second Office Action corresponding to Patent Application CN 201510696298.9 dated Aug. 21, 2019.
Japanese Office Action corresponding to Patent Application JP 2018-516433 dated Aug. 21, 2019.
Chinese First Office Action corresponding to Patent Application CN 201580072284.8 dated Aug. 29, 2019.
Chinese First Office Action corresponding to Patent Application CN 201580073962.2 dated Sep. 5, 2019.
Extended European Search Report corresponding to Patent Application EP 19151805.9 dated Sep. 5, 2019.
Japanese Office Action corresponding to Patent Application JP 2018-537512 dated Sep. 9, 2019.
Extended European Search Report corresponding to Patent Application EP 19170951.8 dated Sep. 26, 2019.
Extended European Search Report corresponding to Patent Application EP 15908020.9 dated Oct. 9, 2019.
Japanese Office Action corresponding to Patent Application JP 2018-534822 dated Oct. 17, 2019.
Extended European Search Report corresponding to Patent Application EP 16884297.9 dated Oct. 31, 2019.
Extended European Search Report corresponding to Patent Application EP 16885490.9 dated Nov. 12, 2019.
Extended European Search Report corresponding to Patent Application EP 19191203.9 dated Dec. 9, 2019.
Extended European Search Report corresponding to Patent Application EP 19191226.0 dated Dec. 10, 2019.
Extended European Search Report corresponding to Patent Application EP 19172130.7 dated Dec. 19, 2019.
European Office Action corresponding to Patent Application EP 18 187 690.5 dated Mar. 23, 2020.
Extended European Search Report corresponding to Patent Application EP 16912243.9 dated Mar. 25, 2020.
Chinese First Office Action corresponding to Patent Application CN 201610694951.2 dated Apr. 23, 2020.
Partial Supplementary European Search Report corresponding to Patent Application EP 18899075.8 dated Jul. 1, 2021.
Australian Examination Report No. 1 corresponding to Patent Application AU 2015413639 dated Jul. 23, 2020.
Chinese First Office Action corresponding to Patent Application CN 201680078525.4 dated Jul. 28, 2020.
Japanese Office Action corresponding to Patent Application JP 2016-217970 dated Sep. 28, 2020.
Extended European Search Report corresponding to Patent Application EP 17895153.9 dated Dec. 17, 2020.
Extended European Search Report corresponding to Patent Application EP 20215391.2 dated Apr. 30, 2021.
Extended European Search Report corresponding to Patent Application EP 18873112.9 dated Oct. 18, 2021.
Extended European Search Report corresponding to Patent Application EP 21164196.4 dated Dec. 17, 2021.
Canadian Office Action dated Sep. 6, 2016 corresponding to Patent Application CA 2,728,538.
Japanese Office Action dated Sep. 1, 2014 corresponding to counterpart Patent Application JP 2011-039024.

* cited by examiner

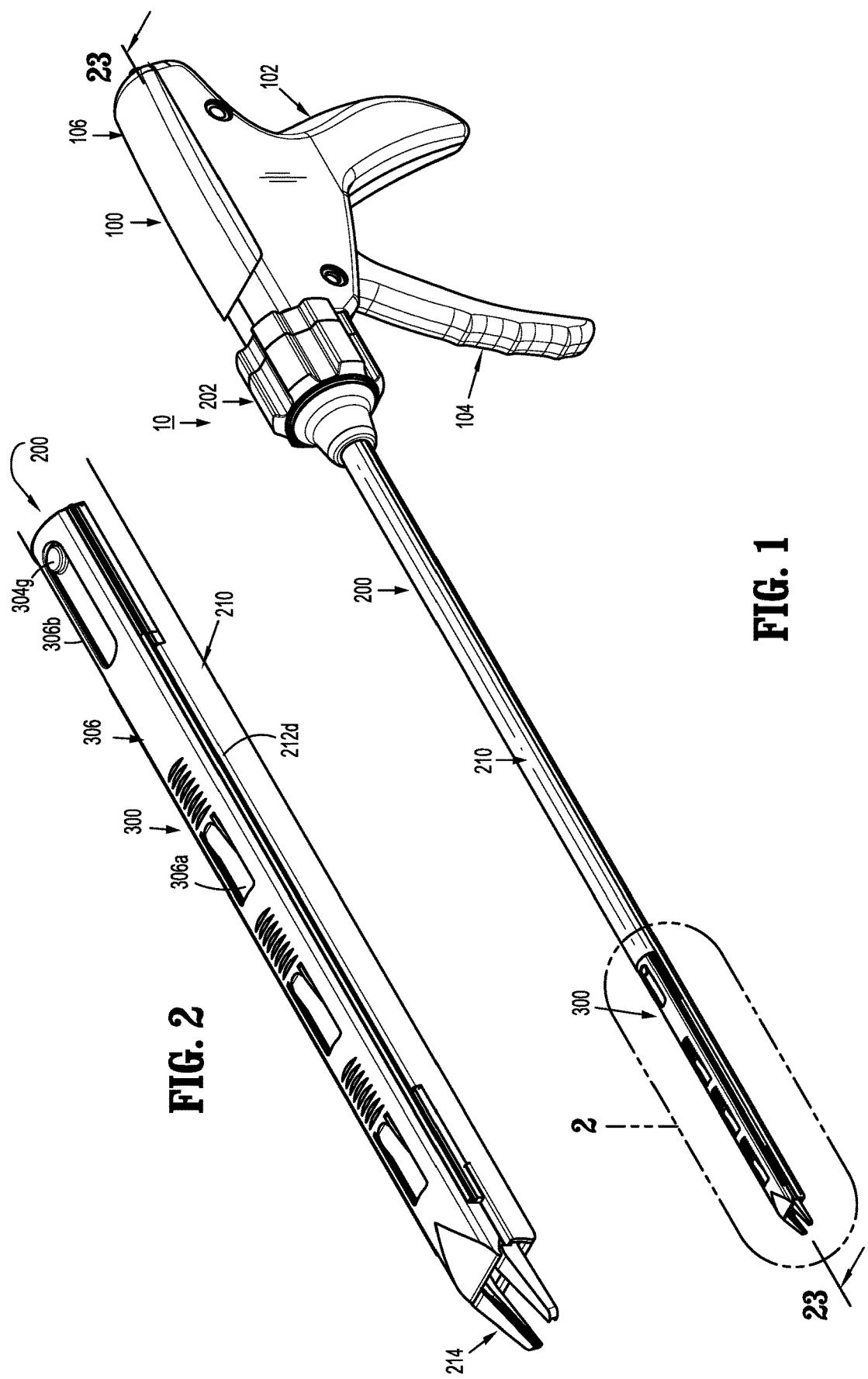

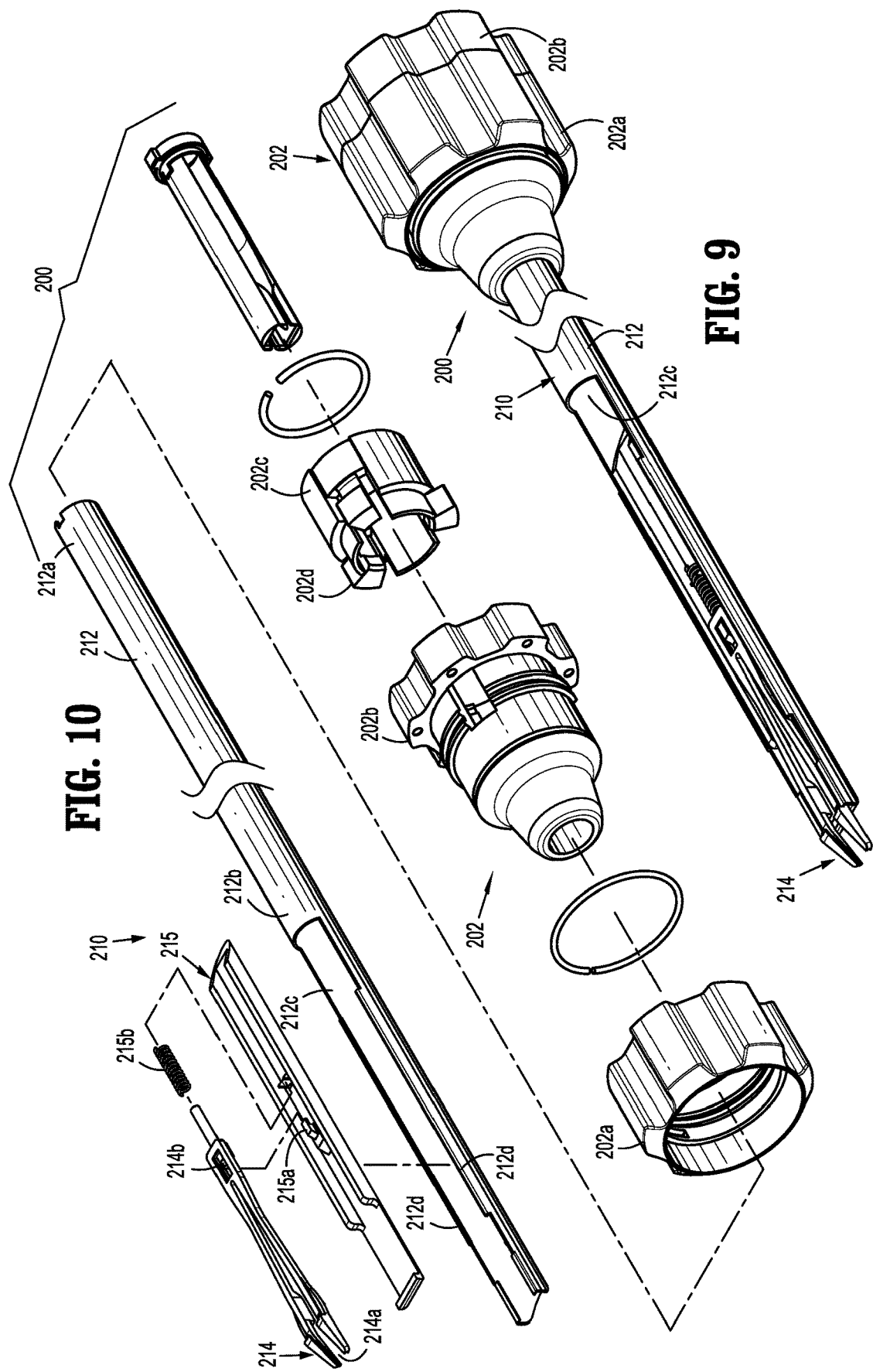

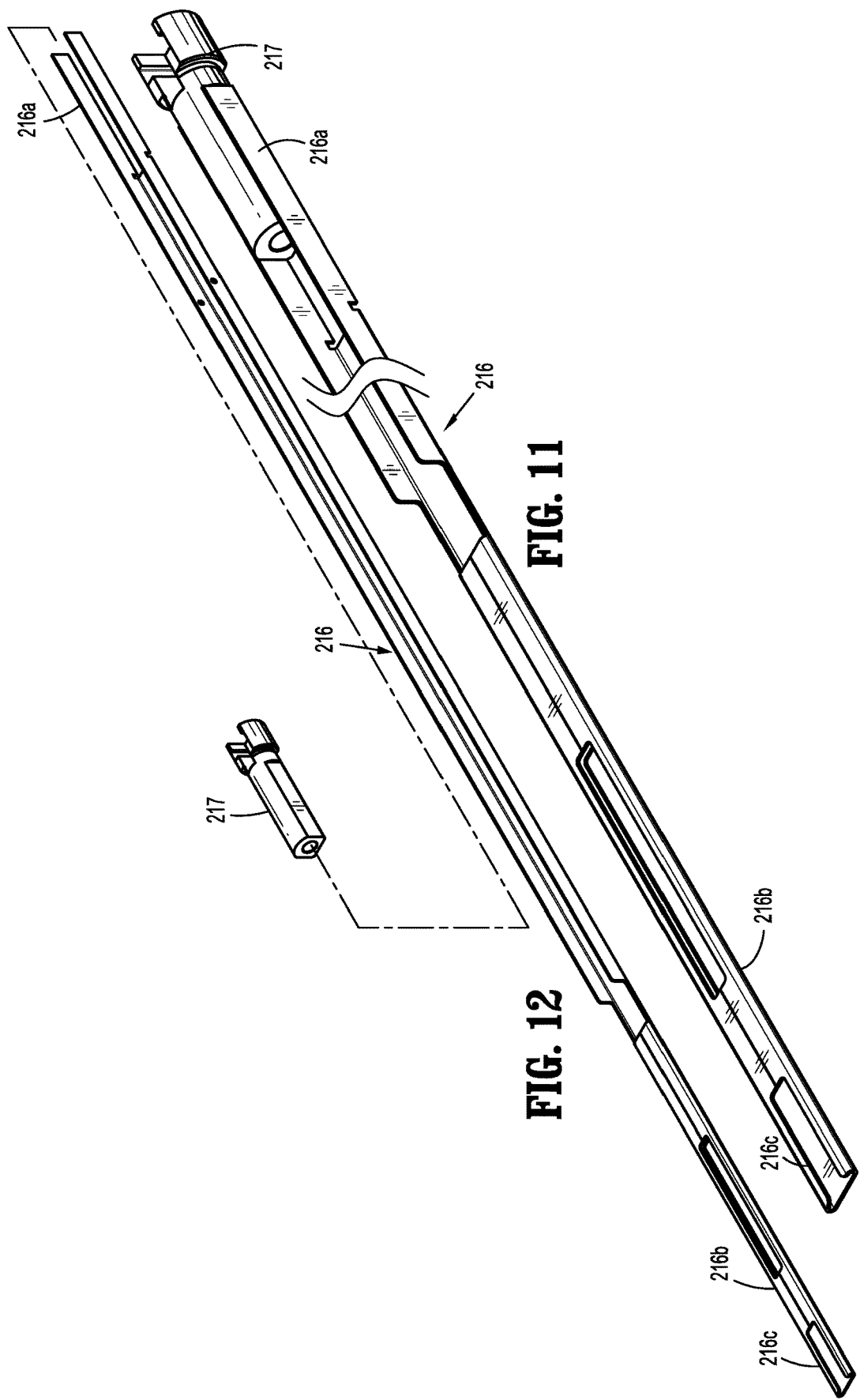

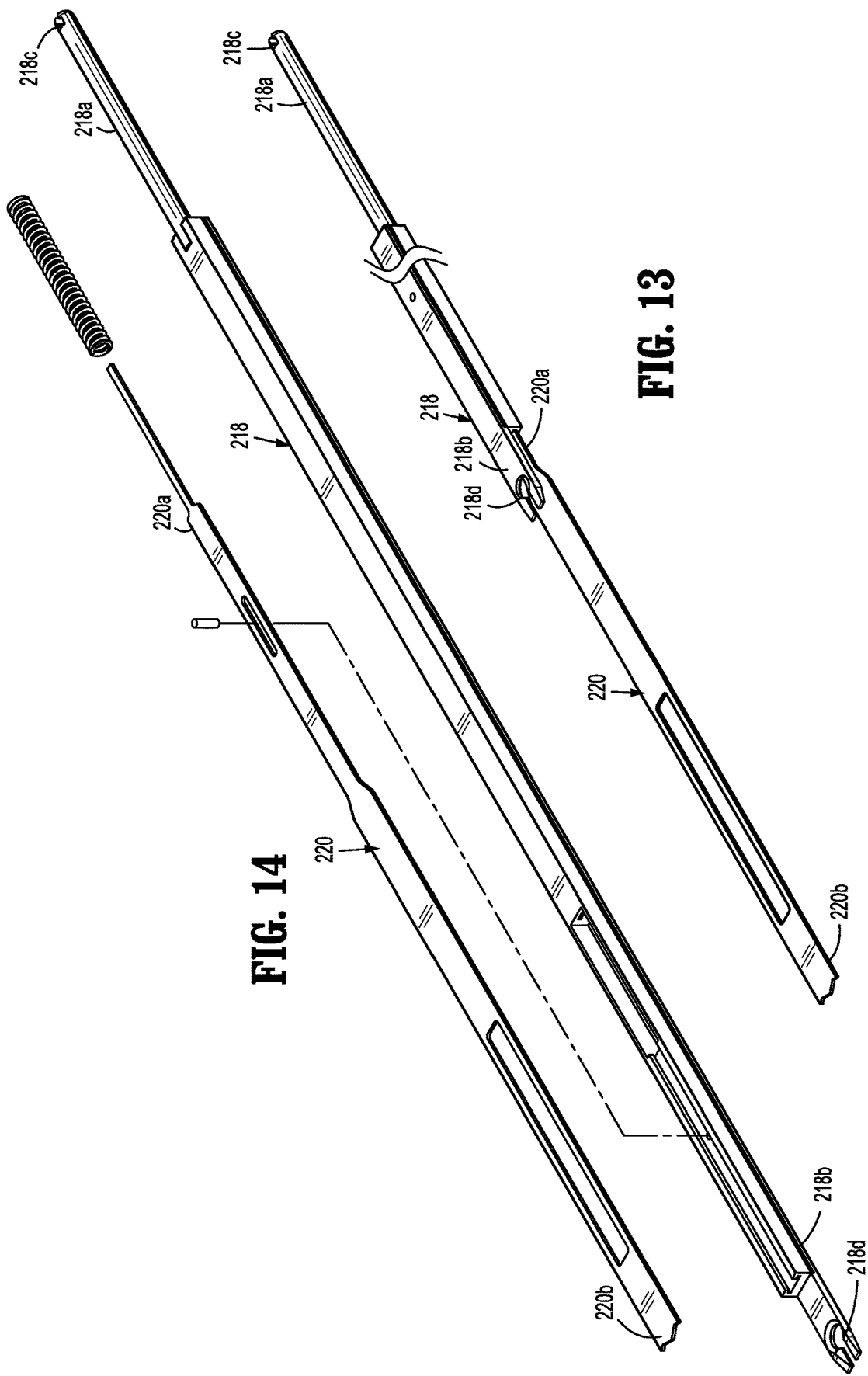

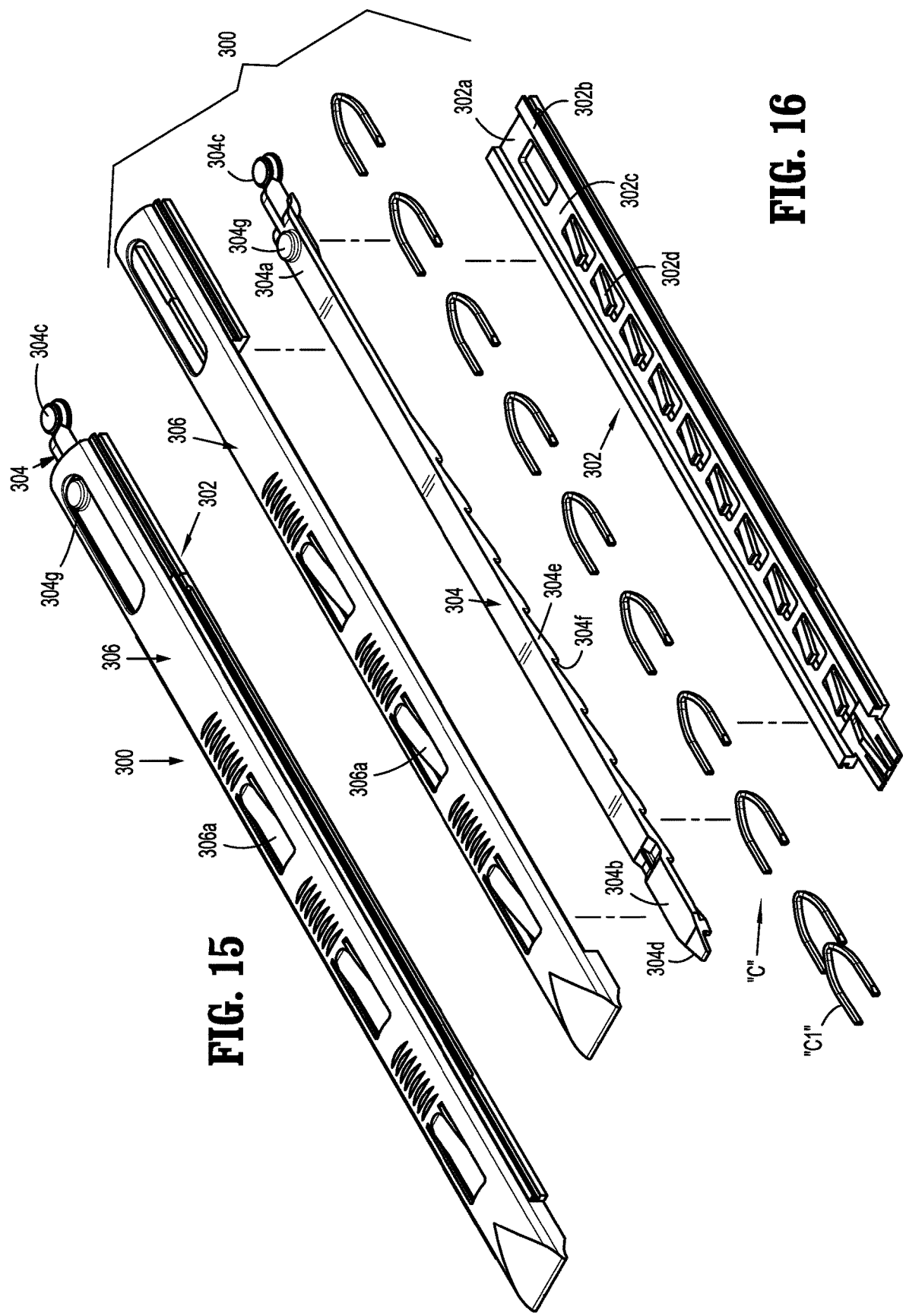

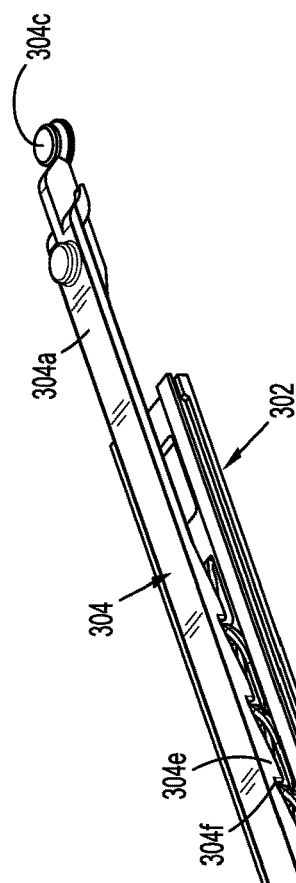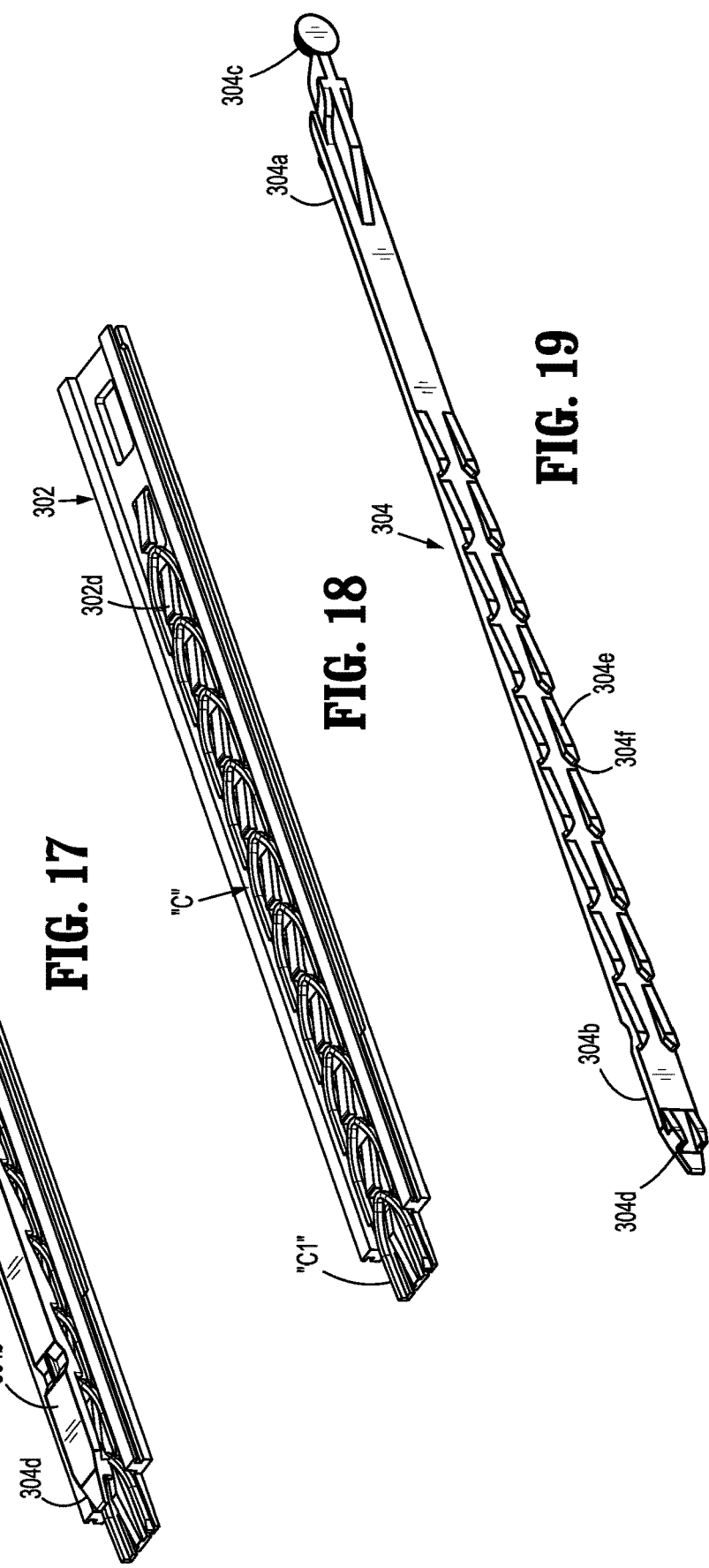

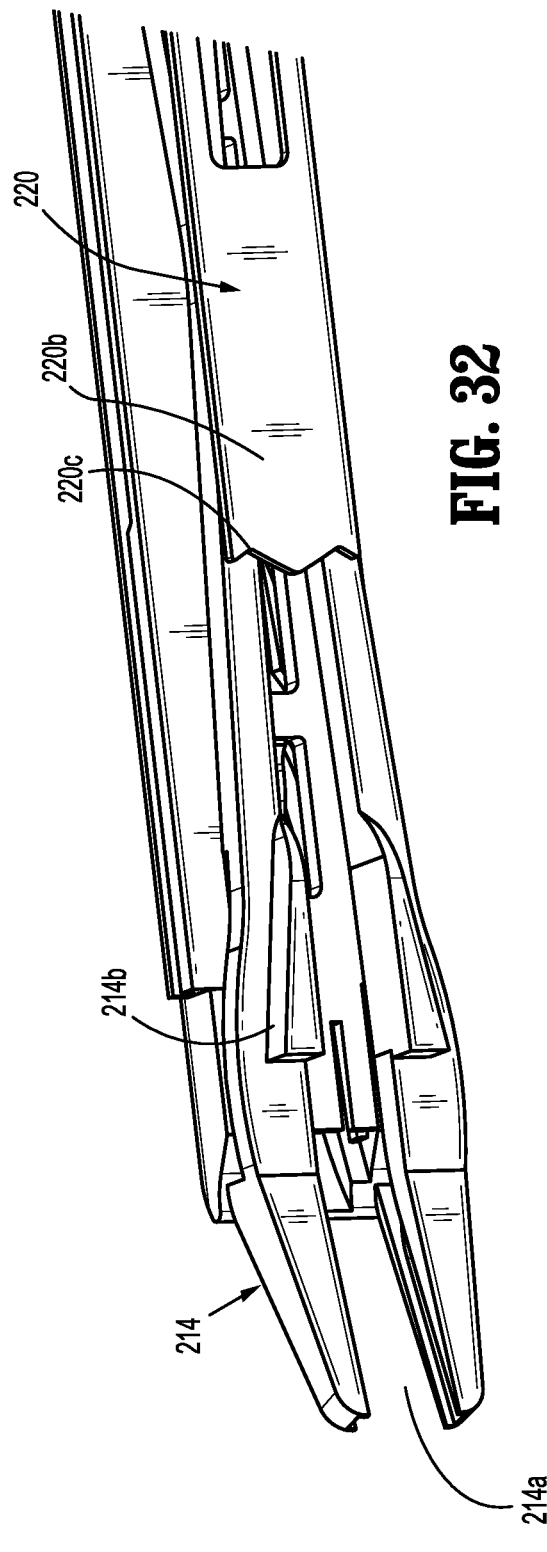
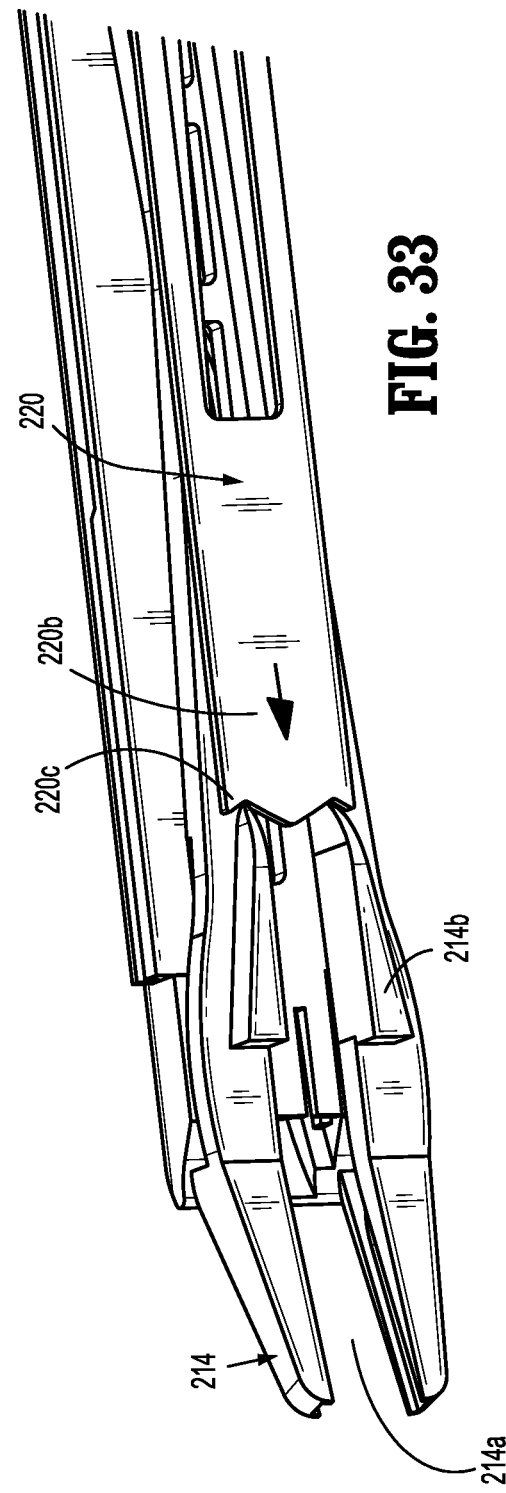

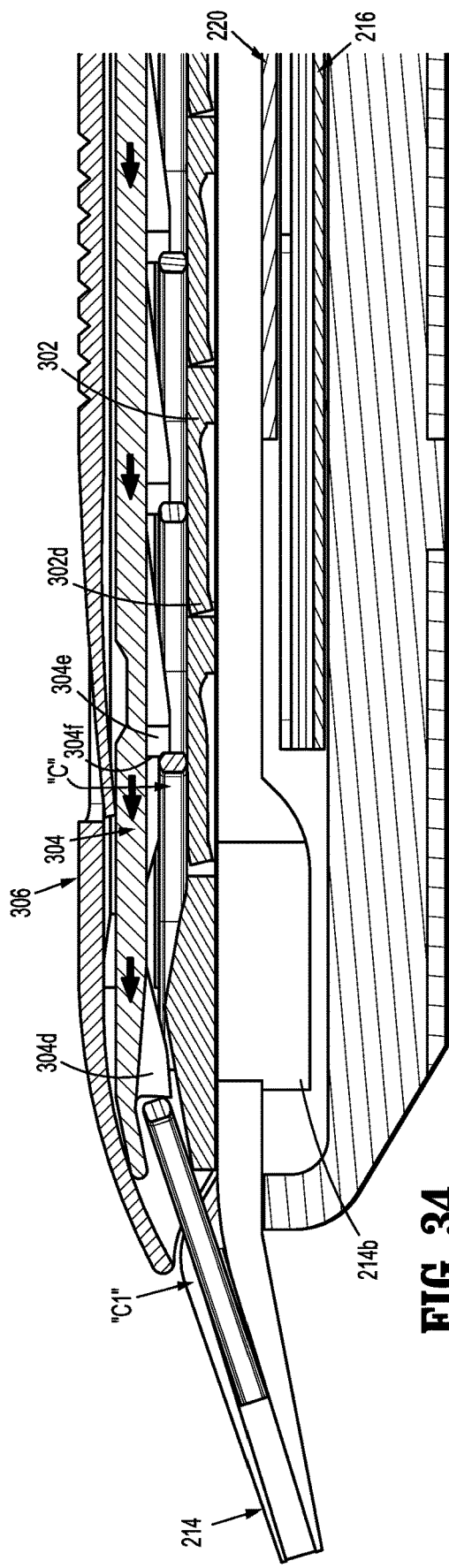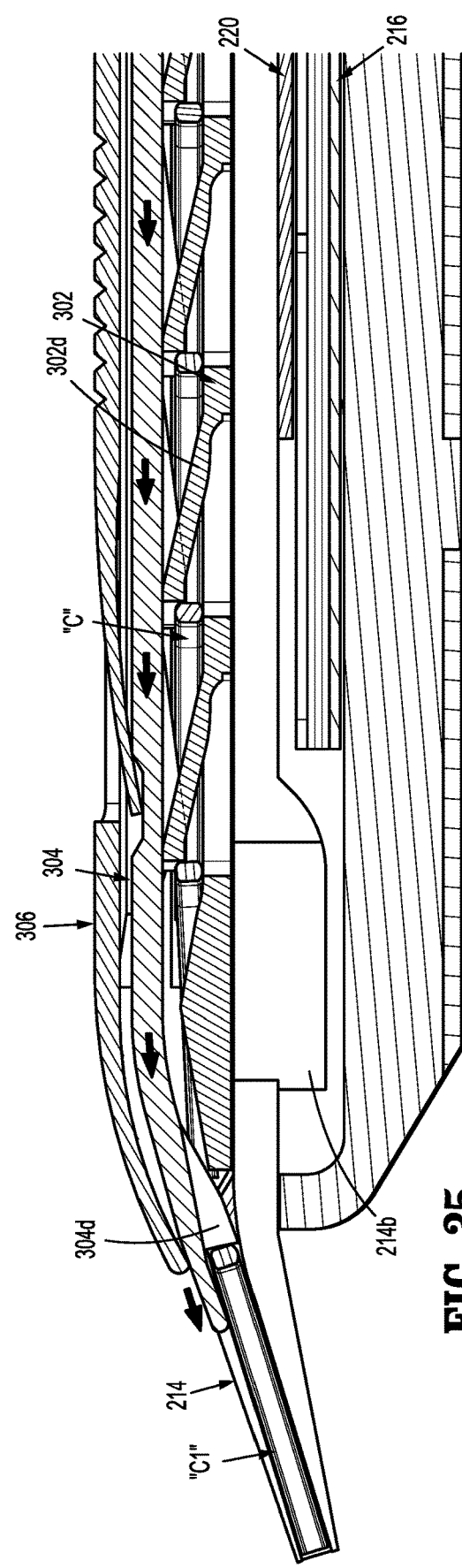

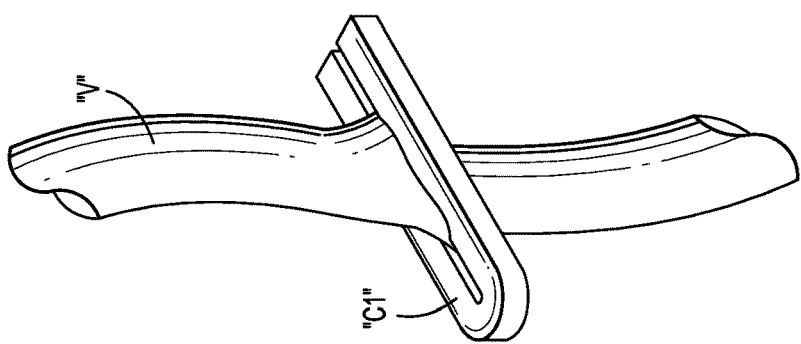
FIG. 38
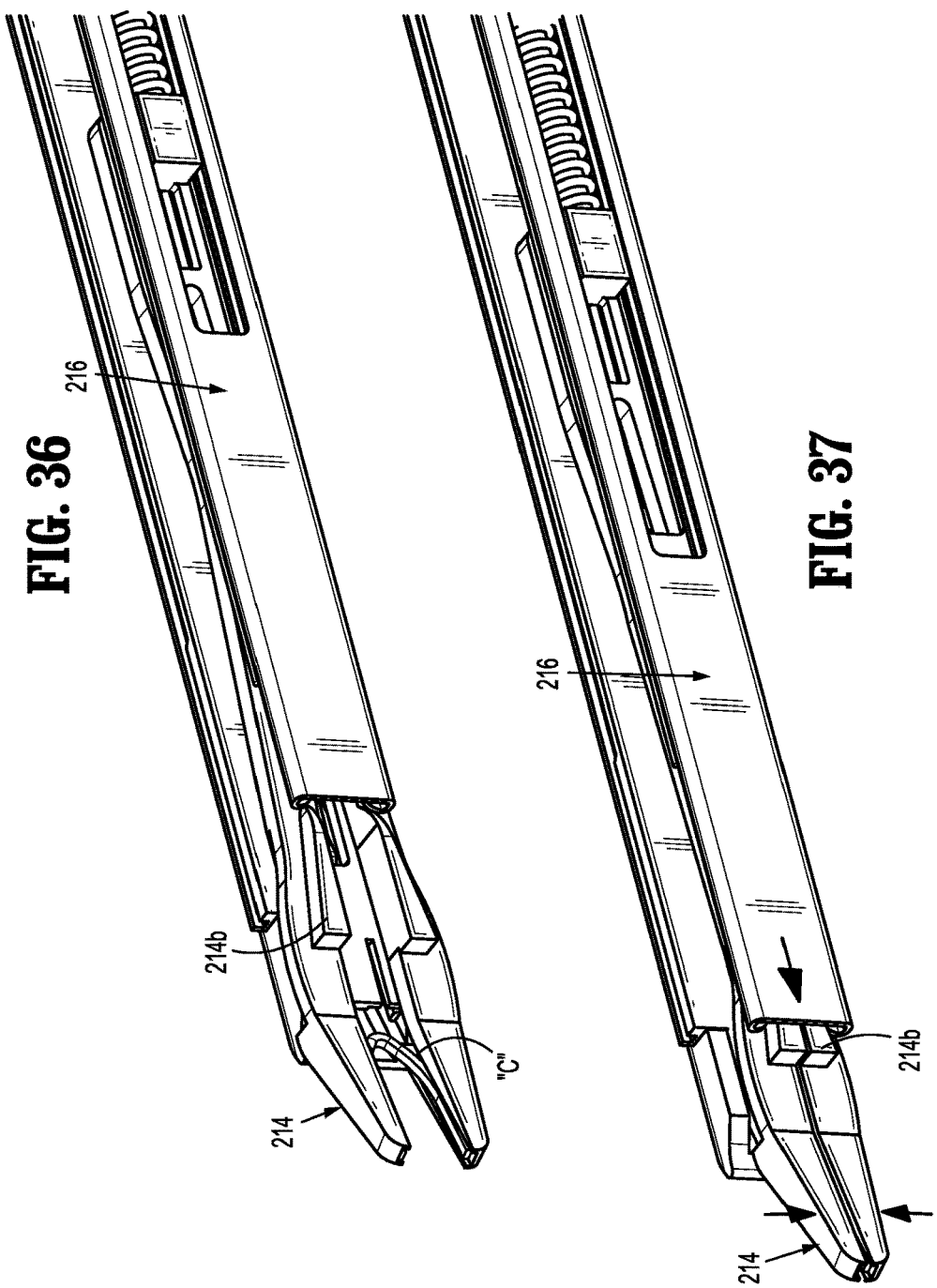
FIG. 36
FIG. 37

ENDOSCOPIC REPOSABLE SURGICAL CLIP APPLIER

CROSS-REFERENCE TO RELATED APPLICATIONS

The present application is a Continuation application which claims the benefit of and priority to U.S. patent application Ser. No. 15/437,059, filed on Feb. 20, 2017; which claims the benefit of and priority to Indian Patent Application Serial No. 201621006379 filed Feb. 24, 2016, the entire content of which is incorporated by reference herein.

BACKGROUND

Technical Field

The technical field relates to surgical clip appliers. More particularly, the present disclosure relates to endoscopic reposable surgical clip appliers having a reusable handle assembly, a reusable shaft assembly, and a disposable clip cartridge assembly.

Description of Related Art

Endoscopic staplers and clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar and for performing surgical procedures far removed from the incision.

During a majority of these procedures, the surgeon must often terminate the flow of blood or another fluid through one or more vessels. The surgeon will often apply a surgical clip to a blood vessel or another duct to prevent the flow of body fluids therethrough during the procedure. An endoscopic clip applier is known in the art for applying a single clip during an entry to the body cavity. Such clips are typically fabricated from a biocompatible material and are usually compressed over a vessel. Once applied to the vessel, the compressed clip terminates the flow of fluid therethrough.

Endoscopic clip appliers that are able to apply multiple clips in endoscopic or laparoscopic procedures during a single entry into the body cavity are described in commonly-assigned U.S. Pat. Nos. 5,084,057 and 5,100,420 to Green et al., which are both incorporated by reference in their entirety. Another multiple endoscopic clip applier is disclosed in commonly-assigned U.S. Pat. No. 5,607,436 by Pratt et al., the contents of which is also hereby incorporated by reference herein in its entirety. These devices are typically, though not necessarily, used during a single surgical procedure. U.S. Pat. No. 5,695,502 to Pier et al., the disclosure of which is hereby incorporated by reference herein, discloses a resterilizable surgical clip applier. The clip applier advances and forms multiple clips during a single insertion into the body cavity. This resterilizable clip applier is configured to receive and cooperate with an interchangeable clip magazine so as to advance and form multiple clips during a single entry into a body cavity.

During endoscopic or laparoscopic procedures it may be desirable and/or necessary to use different size surgical clips depending on the underlying tissue or vessels to be ligated. In order to reduce overall costs of a surgical clip applier, it is desirable for a single surgical clip applier to be loadable with and capable of firing different size surgical clips as needed.

Accordingly, a need exists for endoscopic surgical clip appliers that include reusable handle assemblies, reusable shaft assemblies, and disposable clip cartridge assemblies, with each clip cartridge assembly being loaded with a particularly sized clip (e.g., relatively small, relatively medium, or relatively large).

SUMMARY

The present disclosure relates to reposable endoscopic surgical clip appliers and clip cartridge assemblies suitable for use therewith.

According to an aspect of the present disclosure, a clip cartridge assembly for use with a reposable surgical clip applier is provided and includes a clip tray, a plurality of surgical clips, and a cover.

The clip tray includes a plurality of distally oriented, deflectable, resilient fingers projecting from a base wall thereof. Each resilient finger of the clip tray terminates in a distal shoulder. A proximal end of the clip tray is configured for selective connection with a clip pusher bar of an endoscopic assembly of the reposable surgical clip applier.

The plurality of surgical clips is disposed on the base wall of the clip tray. Each one of the plurality of surgical clips is disposed distally of each respective resilient finger of the clip tray.

The cover includes a plurality of distally oriented, deflectable, resilient fingers projecting within a channel defined through proximal and distal ends thereof. Each resilient finger of the cover terminates in a distal shoulder. The cover includes a pair of opposed slots defined within sidewalls of the channel that are configured to slidably retain the clip tray and the plurality of surgical clips therein. Each one of the plurality of surgical clips is disposed distally of each respective resilient finger of the cover.

In use, upon a distal actuation of the clip tray, the shoulder of each resilient finger of the clip tray may contact a backspan of a respective surgical clip to distally advance all of the surgical clips simultaneously.

Following distal actuation of the clip tray, upon a proximal actuation of the clip tray, the distal shoulder of each resilient finger of the clip tray may contact the backspan of a respective remaining one of the surgical clips to proximally move all the remaining surgical clips until the backspans of the remaining surgical clips contact a respective distal shoulder of the resilient fingers of the cover to block proximal movement of the remaining surgical clips.

The clip tray of the clip cartridge assembly may include at least one through-hole defined through a proximal end thereof. The clip pusher bar of the endoscopic assembly may include a distal coupling for mechanically coupling with the at least one through-hole of the clip tray when the clip cartridge assembly is loaded in the endoscopic assembly.

The clip tray of the clip cartridge assembly may include at least one through-hole defined through a proximal end thereof. The clip pusher bar of the endoscopic assembly may include a distal coupling for mechanically coupling with the at least one through-hole of the clip tray when the clip cartridge assembly is loaded in the endoscopic assembly. The distal coupling of the clip pusher bar of the endoscopic assembly may include at least one boss defined thereon configured to releasably engage the at least one through-hole of the clip tray of the clip cartridge assembly such that depressing the at least one boss disengages the distal coupling of the clip pusher bar of the endoscopic assembly from the clip tray of the clip cartridge assembly.

The outer surface of the cover of the clip cartridge assembly may include a pair of opposed ridges defined thereon configured to releasably engage a corresponding pair of wings defined on the endoscopic assembly.

Each resilient finger of the cover of the cartridge clip assembly may bias the clip tray in a downward direction.

According to another aspect of the present disclosure, a reposable surgical clip applier is provided and includes a handle assembly, an endoscopic assembly selectively connectable to the handle assembly, and a clip cartridge assembly selectively loadable in and connectable to a window defined within the endoscopic assembly.

The clip cartridge assembly includes a clip tray, a plurality of surgical clips, and a cover.

The clip tray includes a plurality of distally oriented, deflectable, resilient fingers projecting from a base wall thereof. Each resilient finger of the clip tray terminates in a distal shoulder. A proximal end of the clip tray is configured for selective connection with a clip pusher bar of the endoscopic assembly of the reposable surgical clip applier.

The plurality of surgical clips is disposed on the base wall of the clip tray. Each one of the plurality of surgical clips is disposed distally of each respective resilient finger of the clip tray.

The cover includes a plurality of distally oriented, deflectable, resilient fingers projecting within a channel defined through proximal and distal ends thereof. Each resilient finger of the cover terminates in a distal shoulder. The cover includes a pair of opposed slots defined within sidewalls of the channel. The pair of opposed slots are configured to slidably retain the clip tray and the plurality of surgical clips therein. Each one of the plurality of surgical clips is disposed distally of each respective resilient finger of the cover.

The handle assembly may include a housing, a trigger pivotally supported on and extending from the housing, and a drive assembly supported within the housing and operatively actuatable by the trigger.

The endoscopic assembly may include a knob assembly configured and adapted for selective connection to the housing of the handle assembly.

The endoscopic assembly may also include an outer tube connected to and extending from the knob assembly. The window of the endoscopic assembly may be defined in a distal end of the outer tube.

The endoscopic assembly may further include a pair of jaws supported in the window of the outer tube and extending from the distal end of the outer tube.

The endoscopic assembly may include a jaw closure bar slidably supported within the outer tube. The jaw closure bar may be operatively connected to the trigger of the handle assembly upon a connection of the endoscopic assembly to the handle assembly.

The clip pusher bar may be slidably supported within the outer tube and operatively connected to the drive assembly of the handle assembly upon a connection of the endoscopic assembly to the handle assembly.

In use, upon a distal actuation of the clip tray, the shoulder of each resilient finger of the clip tray may contact a backspan of a respective clip to distally advance all of the surgical clips simultaneously.

Following distal actuation of the clip tray, upon a proximal actuation of the clip tray, the distal shoulder of each resilient finger of the clip tray may contact the backspan of a respective one of the surgical clips to proximally move all the remaining surgical clips until the backspans of the remaining surgical clips contact a respective distal shoulder of the resilient fingers of the cover to block proximal movement of the remaining surgical clips.

The clip tray of the clip cartridge assembly may include at least one through-hole defined through a proximal end thereof. The clip pusher bar of the endoscopic assembly may include a distal coupling for mechanically coupling with the at least one through-hole of the clip tray when the clip cartridge assembly is loaded in the endoscopic assembly.

The clip tray of the clip cartridge assembly may include at least one through-hole defined through a proximal end thereof. The clip pusher bar of the endoscopic assembly may include a distal coupling for mechanically coupling with the at least one through-hole of the clip tray when the clip cartridge assembly is loaded in the endoscopic assembly.

The distal coupling of the clip pusher bar of the endoscopic assembly may include at least one boss defined thereon configured to releasably engage the at least one through-hole of the clip tray of the clip cartridge assembly such that depressing the at least one boss disengages the distal coupling of the clip pusher bar of the endoscopic assembly from the clip tray of the clip cartridge assembly.

An outer surface of the cover of the clip cartridge assembly may include a pair of opposed ridges defined thereon configured to releasably engage a corresponding pair of wings defined on the window of the endoscopic assembly.

Each resilient finger of the cover of the cartridge clip assembly may bias the clip tray in a downward direction.

The pair of jaws may be removably supported in the window of the outer tube.

The drive assembly of the handle assembly may include a guide block, a proximal unlock member, and a distal unlock member.

The guide block may be operatively connected to the trigger and slidably supported in the housing of the handle assembly.

The proximal unlock member may be pivotally connected to a distal end of the guide block. The proximal unlock member may include a pair of spaced apart distally extending arms. Each arm may include a cam pin extending therefrom and towards one another.

The distal unlock member may be supported in the housing of the handle assembly. The distal unlock member may be slidably disposed between the pair of spaced apart arms of the proximal unlock member. The distal unlock member may include a pair of opposed outwardly projecting cam ramps being in operative registration with the cam pins of the proximal unlock member.

The proximal unlock member and the distal unlock member may be biased in an unactuated position.

The handle assembly may further include a clip pusher bar slidably supported in the housing thereof and a biasing member acting on the clip pusher bar of the handle assembly to urge the clip pusher bar of the handle assembly in the distal direction.

BRIEF DESCRIPTION OF THE DRAWINGS

A particular embodiment of a surgical clip applier is disclosed herein with reference to the drawings wherein:

FIG. 1 is a perspective view of a reposable endoscopic surgical clip applier, according to the present disclosure;

FIG. 2 is an enlarged view of the indicated area of detail of FIG. 1;

FIG. 9 is a perspective view of a shaft assembly of the clip applier of FIGS. 1 and 3;

FIG. 10 is a perspective view, with parts separated, of the shaft assembly of FIG. 9;

FIG. 11 is a perspective view of a jaw pusher assembly of the shaft assembly of FIG. 9;

FIG. 12 is a perspective view, with parts separated, of the jaw pusher assembly of FIG. 11;

FIG. 13 is a perspective view of a clip pusher assembly of the shaft assembly of FIG. 9;

FIG. 14 is a perspective view, with parts separated, of the clip pusher assembly of FIG. 13;

FIG. 15 is a perspective view of a surgical clip cartridge assembly;

FIG. 16 is a perspective view, with parts separated, of the clip cartridge assembly of FIG. 15;

FIG. 17 is a perspective view of the clip cartridge assembly of FIGS. 14-15 with a cover removed therefrom;

FIG. 18 is a perspective view of the clip cartridge assembly of FIGS. 14-15 with a cover and a clip pusher removed therefrom;

FIG. 19 is a perspective view of a clip pusher of the clip cartridge assembly of FIGS. 14-15;

FIGS. 32 and 33 are perspective views of a clip logic feature of the clip pusher bar acting on a pair of jaws of the clip applier;

FIGS. 34 and 35 are longitudinal, cross-sectional views illustrating a loading of a distal-most surgical clip into the pair of jaws of the clip applier;

FIGS. 36 and 37 are perspective views of the jaw closure bar acting on the pair of jaws of the clip applier to close the jaws and form a clip loaded therein; and FIG. 38 is a perspective view of a surgical clip formed on a vessel.

DETAILED DESCRIPTION OF EMBODIMENTS

Figure 3:
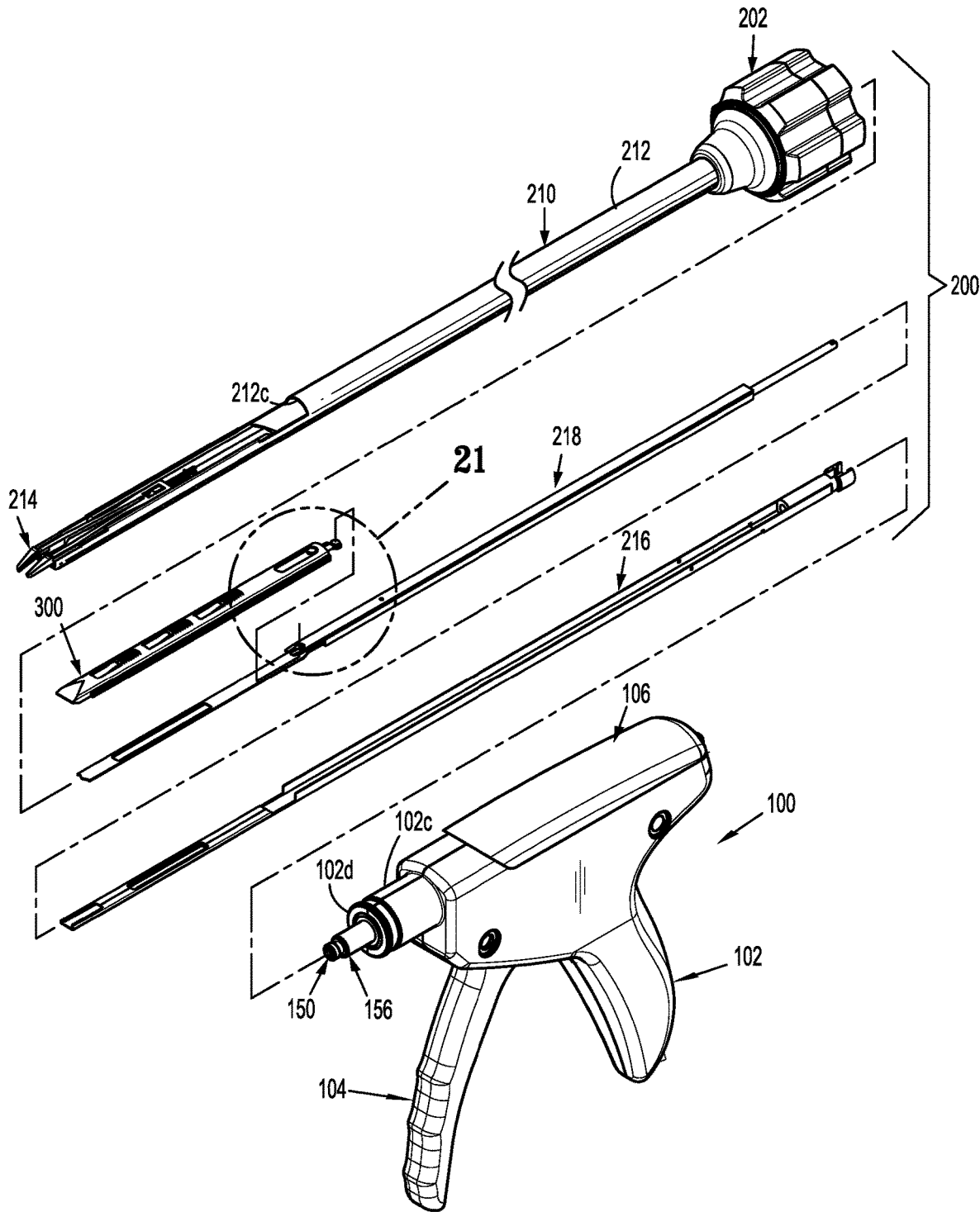
FIG. 3 is a perspective view, with parts separated, of the clip applier of FIG. 1.

Embodiments of reposable endoscopic surgical clip appliers, in accordance with the present disclosure, will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Referring now to FIGS. 1-37, an endoscopic surgical clip applier in accordance with an embodiment of the present disclosure is generally designated as 10. Surgical clip applier 10 generally includes a handle assembly 100, an endoscopic assembly 200 including a shaft assembly 210 selectively connectable to and extendable distally from handle assembly 100; and at least one surgical clip cartridge assembly 300 selectively loadable into shaft assembly 210 of endoscopic assembly 200.

Briefly, shaft assembly 210 of endoscopic assembly 200 may have various outer diameters such as, for example, about 5 mm or about 10 mm, depending on intended use. Further, shaft assembly 210 may have various relatively elongated or shortened lengths depending on intended use, such as, for example, in bariatric surgery. In one embodiment, in bariatric surgery, shaft assembly 210 may have a length of between about 30 cm and about 40 cm. However one skilled in the art should appreciate that shaft assembly 210 may have any length in excess of about 30 cm and the present disclosure is not limited to any of the above identified lengths.

In accordance with the present disclosure, as will be discussed in greater detail below, each surgical clip cartridge assembly 300 may be loaded with a particularly sized set of surgical clips (e.g., relatively small surgical clips, relatively medium surgical clips, or relatively large surgical clips). Each clip cartridge assembly 300 is configured to be selectively loaded into shaft assembly 210 of endoscopic assembly 200, and to be actuated by handle assembly 100 to fire and form the surgical clips loaded therein onto underlying tissue and/or vessels.

Referring now to FIGS. 1-8, handle assembly 100 of surgical clip applier 10 is shown. Handle assembly 100 includes a housing 102 having a first or right side half-section 102a and a second or left side half-section 102b. Handle assembly 100 includes a trigger 104 pivotably supported between right side half-section 102a and left side half-section 102b of housing 102. Trigger 104 is biased by a biasing member 104a (e.g., a spring) to an un-actuated condition.

Figure 4:
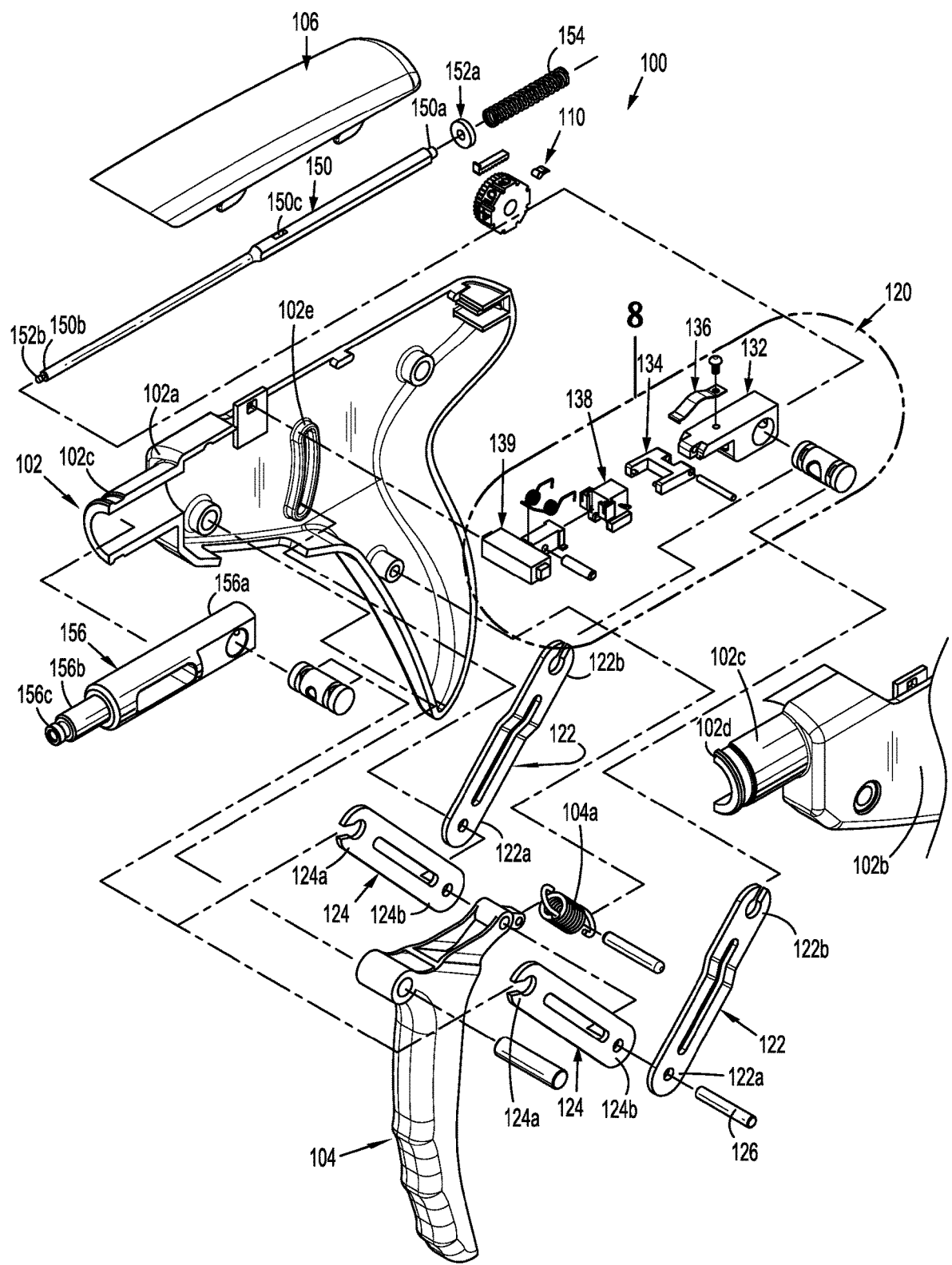
FIG. 4 is a perspective view, with parts separated, of a handle assembly of the clip applier of FIGS. 1 and 3.
Figure 5:
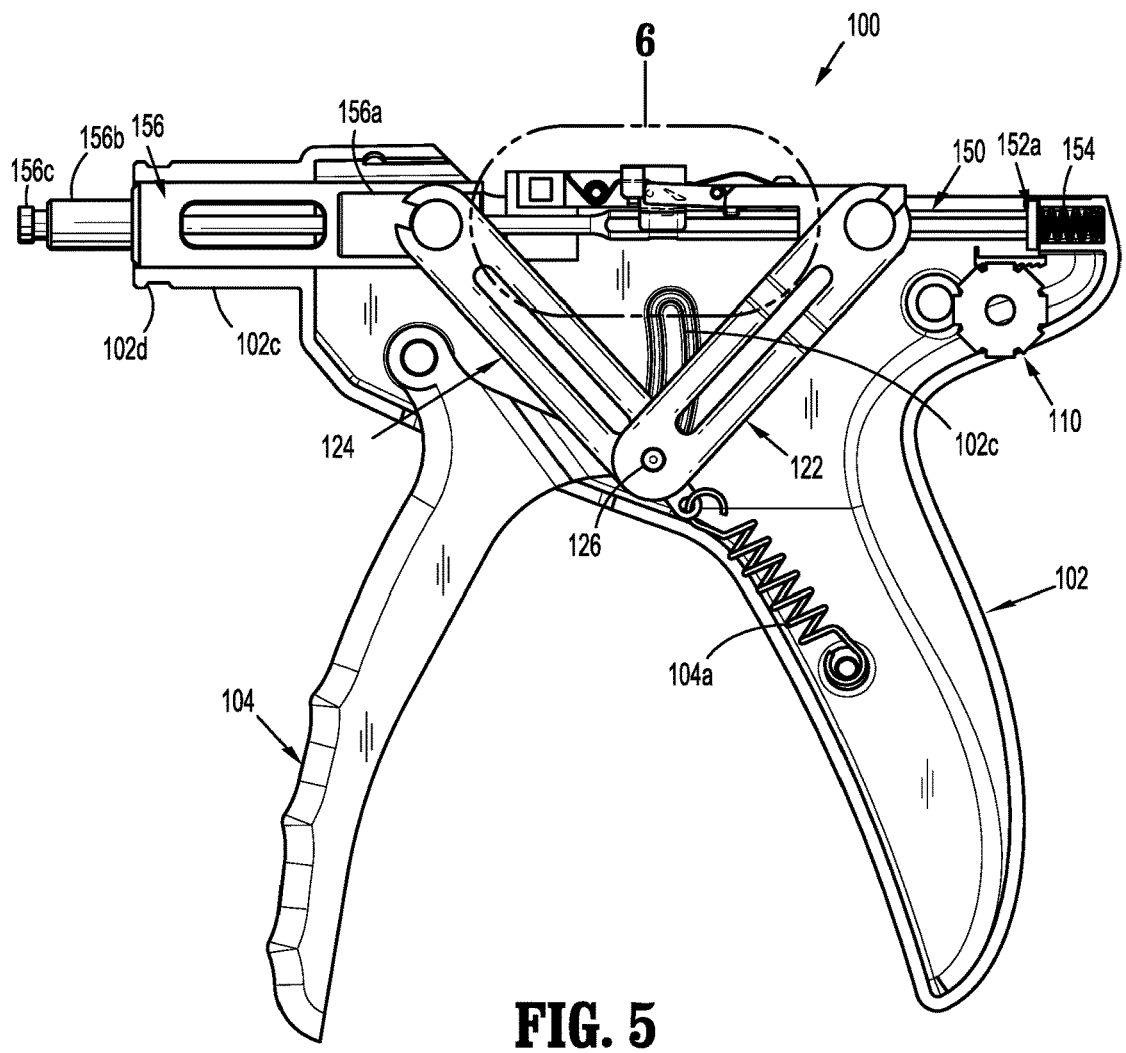
FIG. 5 is a side, elevational view of the handle assembly of FIG. 4, with a housing half-section removed therefrom.
Figure 6:
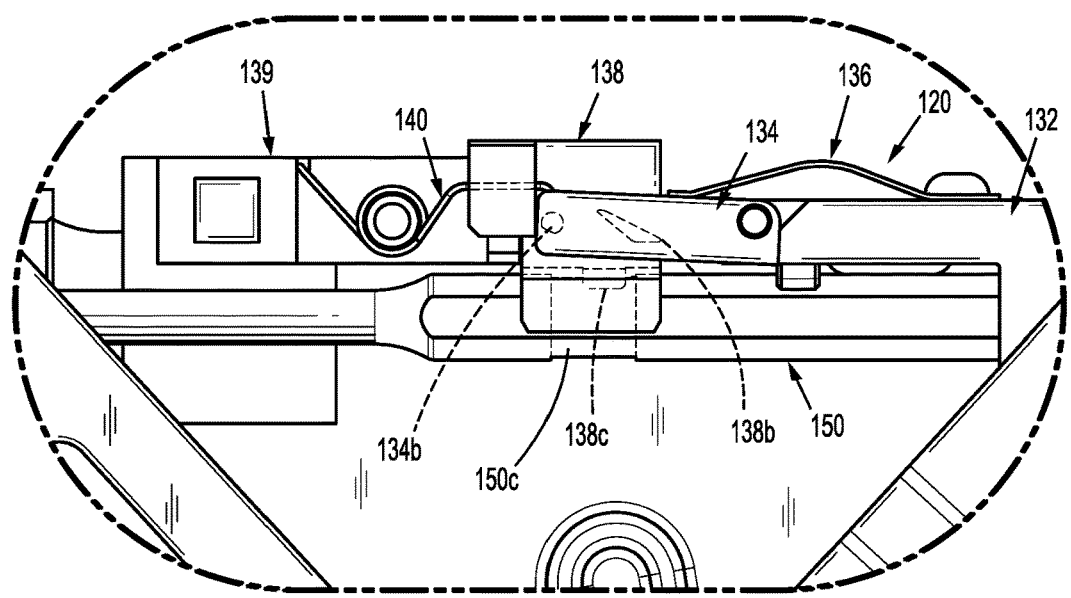
FIG. 6 is an enlarged view of the indicated area of detail of FIG. 5.
Figure 7:
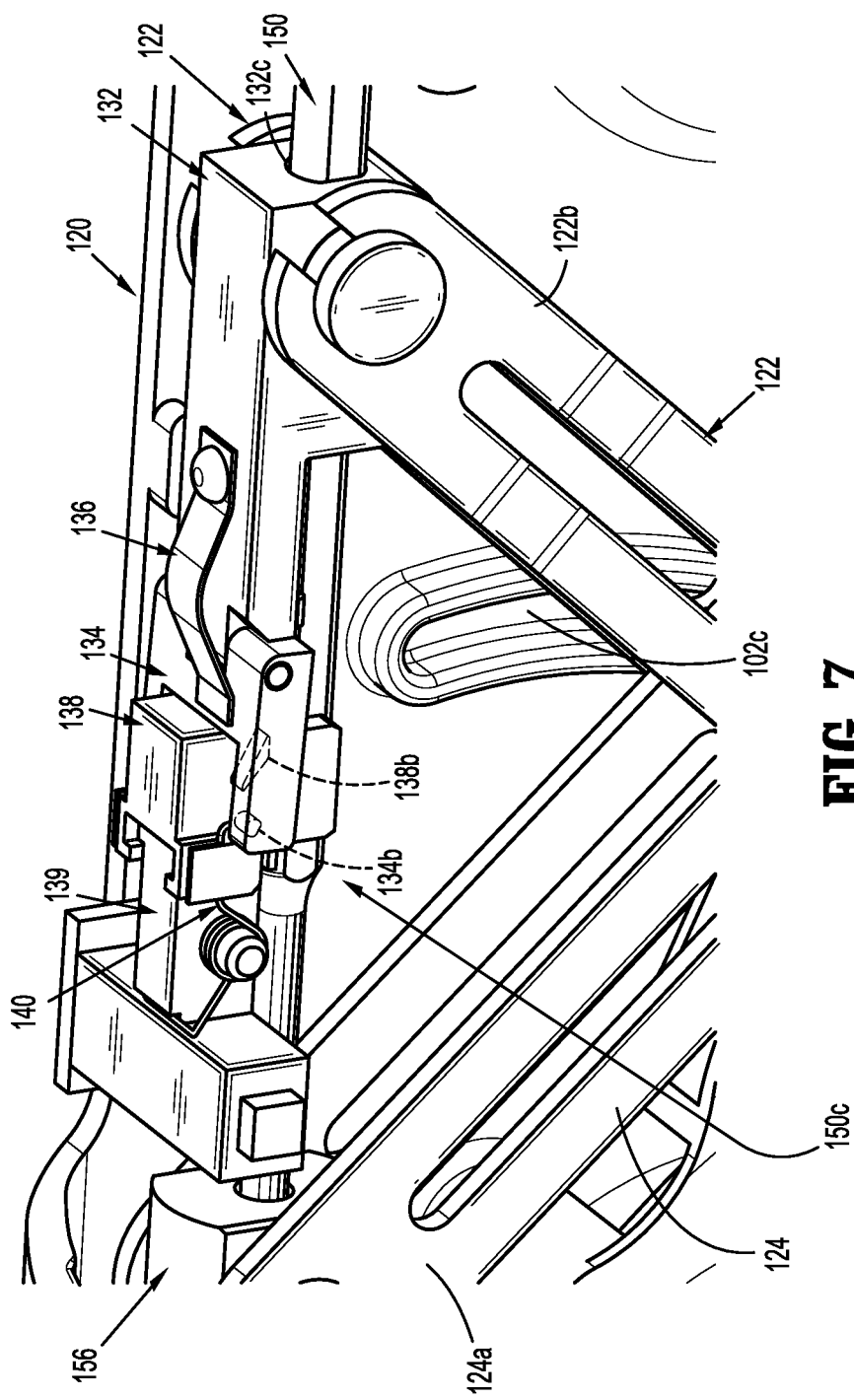
FIG. 7 is an enlarged, perspective view of a drive assembly of the handle assembly of FIGS. 5-6.
Figure 8:
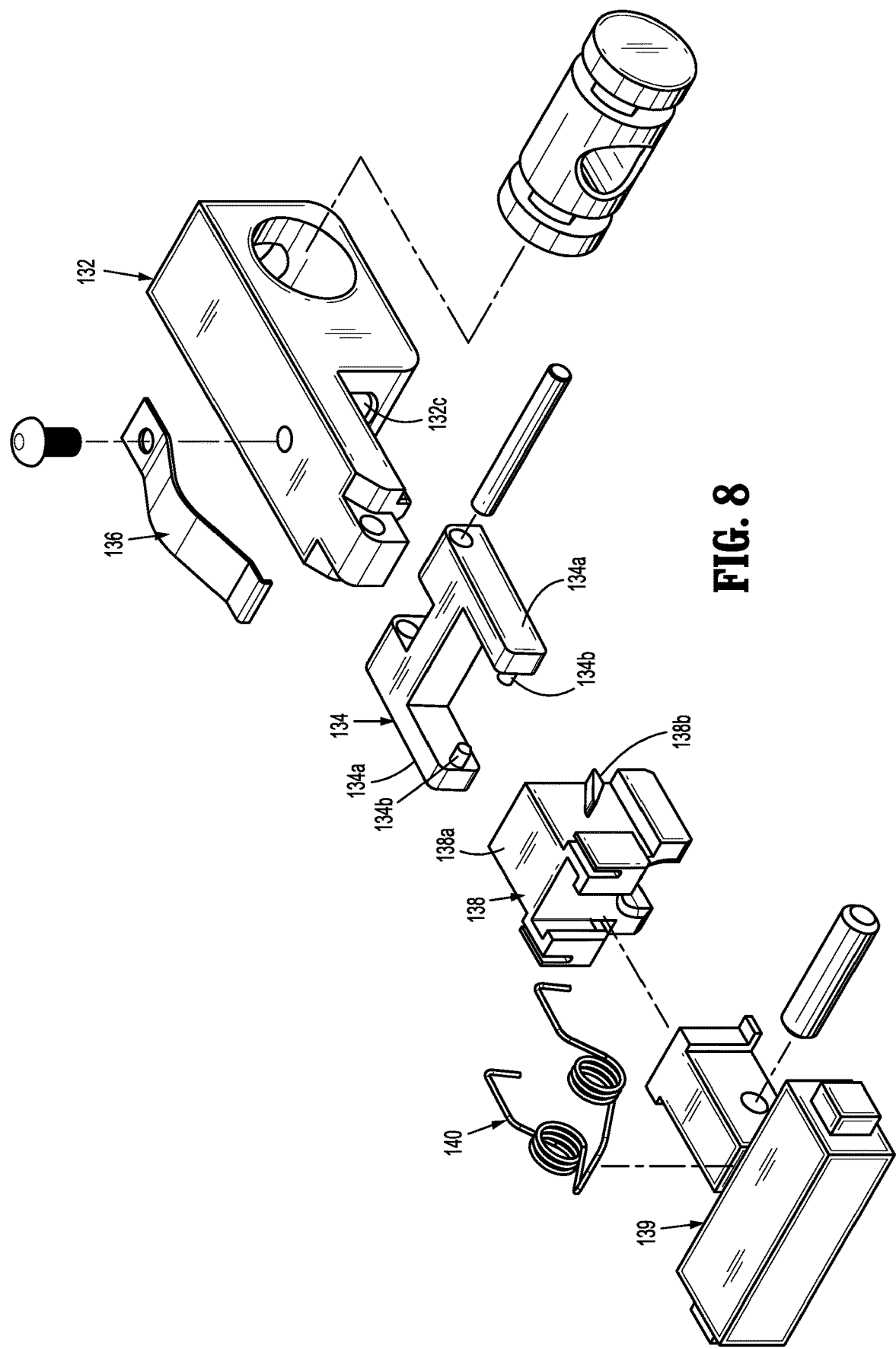
FIG. 8 is a perspective view, with parts separated of the drive assembly of FIG. 7.

Housing 102 of handle assembly 100 may be formed of a suitable plastic or thermoplastic material. Handle assembly 100 includes a removable cover 106 or the like which provides access to a drive assembly 120 of clip applier 10. Housing 102 of handle assembly 100 further includes, as seen in FIGS. 3-5, a nose 102c defining an annular flange 102d.

Handle assembly 100 includes a drive assembly 120 operatively connected to trigger 104. Specifically, drive assembly 120 includes a proximal linkage (or pair of linkages) 122, and a distal linkage 124. Proximal linkage 122 includes a distal coupling portion 122a pivotally connected to trigger 104, and a proximal coupling portion 122b pivotally connected to a guide block 126. Distal linkage 124 includes a distal coupling portion 124a pivotally connected to a jaw pusher tube or cylinder 156, and a proximal coupling portion 124b pivotally connected to trigger 104. A pin 126 pivotally connects proximal linkage 122 and distal linkage 124 to trigger 104. Pin 126 is also slidably disposed within opposed arcuate channels 102c formed in opposed handle half-sections 102a, 102b. In this manner, as trigger 104 is actuated, pin 126 rides along slot 102e (FIG. 4), and causes opposed proximal coupling portion 122b of proximal linkage 122 and distal coupling portion 124a of distal linkage 124 to separate from one another.

As seen in FIGS. 4-8, drive assembly 120 further includes a guide block 132 defining a longitudinally extending passage 132a therethrough. Proximal coupling portion 122b of proximal linkage 122 is pivotally connected to guide block 132.

Drive assembly 120 further includes a proximal unlock member 134 pivotally connected to a distal portion of guide block 132. Proximal unlock member 134 includes a pair of distally oriented, spaced apart arms 134a, with each arm 134a including a cam pin 134b extending therefrom and towards one another. A biasing member 136 (e.g., a leaf spring) is provided and includes a first end secured to guide block 132, and a free end acting on proximal unlock member 134 to exert a force on proximal unlock member 134 and maintain proximal unlock member 134 in a locked position, as will be discussed in greater detail below.

Drive assembly 120 additionally includes a distal unlock member 138 pivotally supported in housing 102 of handle assembly 100, such as, for example, by a support block 139 or the like. Alternatively, distal unlock member 138 may be directly pivotally connected to housing 102 of handle assembly 100. Distal unlock member 138 includes a nose portion 138a (FIG. 8) configured and dimensioned for disposition between spaced apart arms 134a of proximal unlock member 134. Distal unlock member 138 includes a pair of cam ramps 138b extending from opposed sides of nose portion 138a of distal unlock member 138. Cam ramps 138b of distal lock member 138 are in operative association with cam pins 134b of proximal unlock member 134, as will be described in greater detail below. Distal unlock member 138 further includes a lock tab 138c projecting therefrom and extending towards a clip pusher bar 150 (see FIGS. 6, 26 and 31), for selective engagement with clip pusher bar 150, as will be described in greater detail below. A biasing member 140 (e.g., a coil spring or the like) is provided and includes a first end secured to support block 139, and a free end acting on distal unlock member 138 to exert a force on distal unlock member 138 and maintain distal unlock member 138 in a locked position, as will be described in greater detail below.

With continued reference to FIGS. 4-8, drive assembly 120 includes a clip pusher bar 150 slidably supported within and through housing 102 of handle assembly 100. Clip pusher bar 150 includes a flange 152a supported on a proximal end 150a thereof, and a coupling tip 152b formed at a distal end 150b thereof. Clip pusher bar 150 is dimensioned such that coupling tip 152b thereof projects from nose 102c of housing 102 of handle assembly 100. Clip pusher bar 150 defines a window or slot 150c therein for selective receipt of lock tab 138c of distal unlock member 138 (FIGS. 6 and 26), as will be described in greater detail below. A biasing member 154 (e.g., a compression spring) is interposed between housing 102 of handle assembly 100 and flange 152a of clip pusher bar 150. Biasing member 154 acts on clip pusher bar 150 to bias or urge clip pusher bar 150 in a distal direction.

When clip pusher bar 150 is in a proximal position, lock tab 138c of distal unlock member 138 is disposed within window or slot 150c of clip pusher bar 150, and biasing member 154 is compressed between housing 102 of handle assembly 100 and flange 152a of clip pusher bar 150.

Drive assembly 120 further includes a jaw pusher tube 156 slidably supported within housing 102 of handle assembly 100. Jaw pusher tube 156 defines a lumen therethrough for receipt of and slidable passage of clip pusher bar 150 therein. Jaw pusher tube 156 includes a proximal end 156a pivotally connected to distal coupling portion 124a of distal linkage 124, and a coupling tip 156c formed at a distal end 156b thereof. Jaw pusher tube 156 is dimensioned such that coupling tip 156c thereof projects from nose 102c of housing 102 of handle assembly 100.

Turning now to FIGS. 1-3 and 9-10, endoscopic assembly 200 of surgical clip applier 10 is shown. Endoscopic assembly 200 includes a knob assembly 202 configured for selective connection to annular flange 102d of nose 102c of housing 102 of handle assembly 100. Knob assembly 202 includes an outer knob collar 202a, an inner knob collar 202b configured for receipt in outer knob collar 202a, and a lock collar 202c configured for receipt in inner knob collar 202b.

In use, when outer knob collar 202a is in a first position relative to inner knob collar 202b, knob assembly 202 may be coupled onto or may receive nose 102c of housing 102 of handle assembly 100. When outer knob collar 202a is in a second position relative to inner knob collar 202b, with nose 102c of housing 102 disposed within lock collar 202c of knob assembly 202, outer knob collar 202a acts on tabs 202d of lock collar 202c to urge tabs 202d into annular flange 102d of nose 102c of housing 102, to lock endoscopic assembly 200 onto handle assembly 100.

Knob assembly 202 may be rotatably mounted on nose 102c of housing 102 to transmit and/or provide 360° rotation to shaft assembly 210 and to a pair of jaws 214 about a longitudinal axis thereof.

As shown in FIGS. 1-3 and 9-14, endoscopic assembly 200 includes a shaft assembly 210 extending from knob assembly 202. Shaft assembly 210 includes an outer tube 212 having a proximal end portion 212a fixedly secured to inner knob collar 202b of knob assembly 202, and a distal end portion 212b extending from inner knob collar 202b of knob assembly 202. Distal end portion 212b of outer tube 212 defines a channel or window 212c formed in a side thereof.

Figure 20:
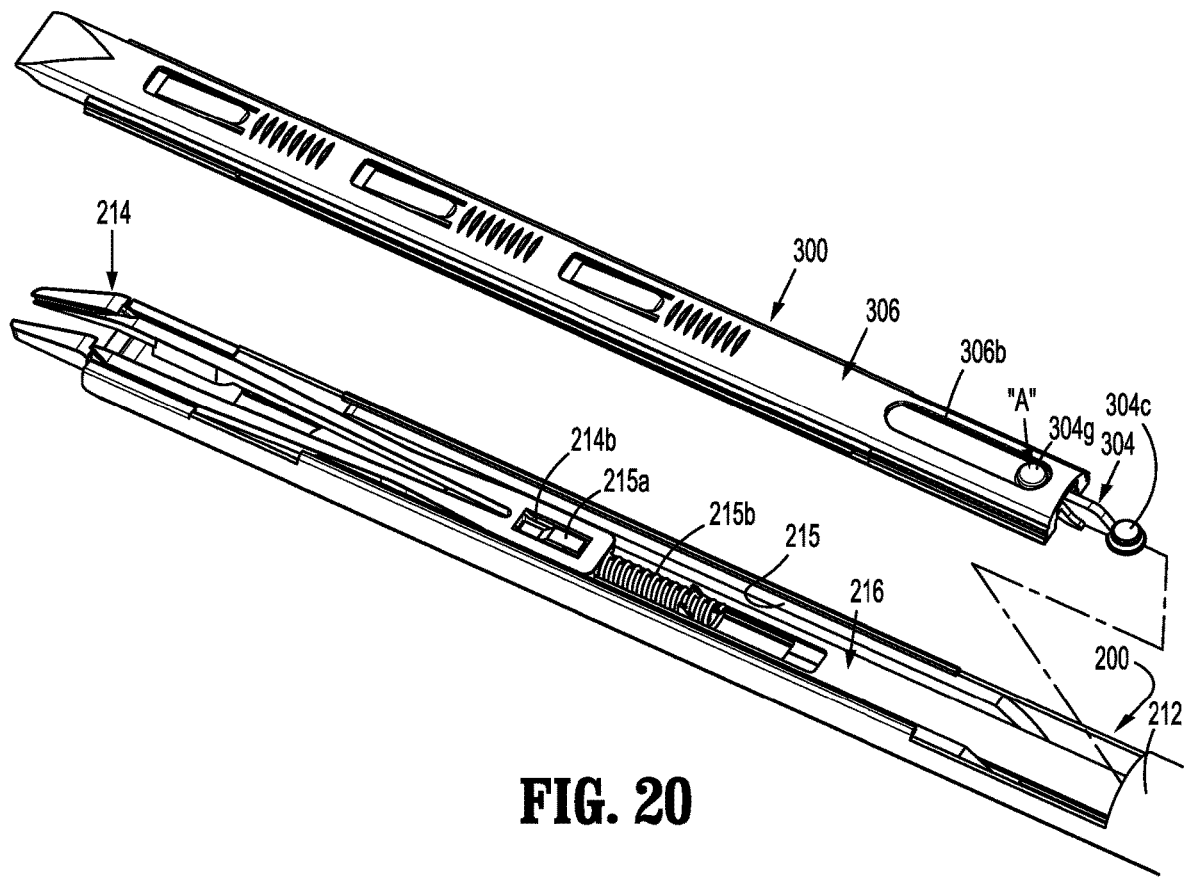
FIG. 20 is a perspective view illustrating a loading of the clip cartridge assembly to or with the shaft assembly.
Figure 29:
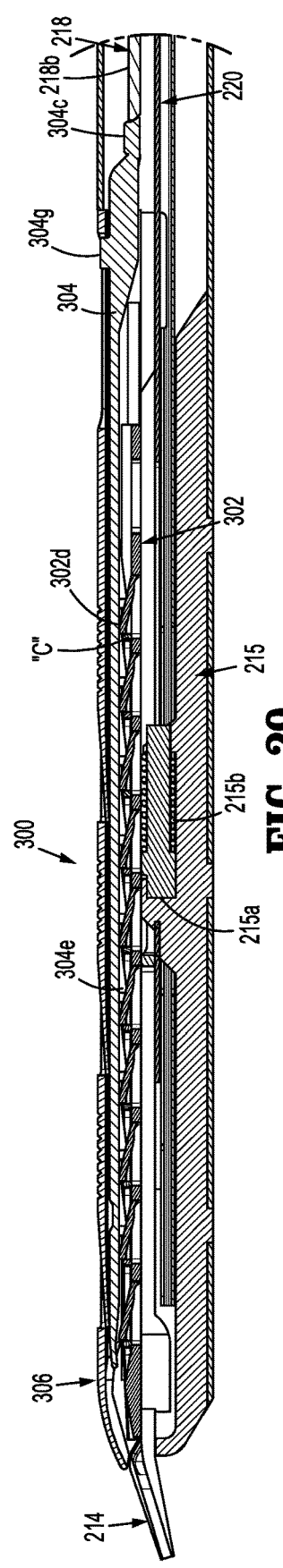
FIG. 29 is an enlarged view of the indicated area of detail of FIG. 28.

Shaft assembly 210 includes a pair of jaws 214 mounted in channel 212c of outer tube 212 and actuatable by an actuation of trigger 104 of handle assembly 100. The pair of jaws 214 is formed of a suitable biocompatible material such as, for example, stainless steel or titanium. The pair of jaws 214 is removably mounted in channel 212c of outer tube 212. With reference to FIGS. 10, 20 and 29, the pair of jaws 214 may be disposed on a mounting tooth 215a projecting from a tube filler 215 that is fixedly mounted or supported in channel or window 212c of outer tube 212 of endoscopic assembly 200. In particular, the pair of jaws 214 may define a window 214c formed in a shank portion 214b thereof, wherein window 214c of the pair of jaws 214 receives mounting tooth 215a therein when the pair of jaws 214 is mounted in channel 212c of outer tube 212. A biasing member 215b is provided to maintain the pair of jaws 214 engaged with the mounting tooth 215a.

Referring momentarily to FIGS. 32, 33, 36 and 37, the pair of jaws 214 defines a channel 214a therebetween for receipt of a surgical clip "C" therein. The pair of jaws 214 include a pair of camming wedge surfaces 214b projecting therefrom. As will be described in detail below, the pair of camming wedge surfaces 214b is acted upon by a jaw closure bar 216 to actuate the pair of jaws 214 to a closed position.

With reference to FIGS. 3 and 9-13, shaft assembly 210 includes a jaw closure bar 216 slidably supported within outer tube 212. Jaw closure bar 216 includes a proximal end portion 216a fixedly supporting a coupling hub 217, and a distal end portion 216b configured to engage and act on the pair of jaws 214. Specifically, distal end portion 216b of jaw closure bar 216 defines a distally, open-ended channel 216c configured and dimensioned to engage the outer surfaces of the pair of camming wedge surfaces 214b of the pair of jaws 214 as the jaw closure bar 216 is moved in a distal direction, relative to the pair of jaws 214, to approximate the pair of jaws 214.

Coupling hub 217 of jaw closure bar 216 is configured to selectively connect to coupling tip 156c of jaw pusher tube 156 of drive assembly 120 of handle assembly 100. In use, with coupling hub 217 of jaw closure bar 216 connected to coupling tip 156c of jaw pusher tube 156, axial translation of jaw pusher tube 156 results in axial translation of jaw pusher tube 156. It is contemplated that coupling hub 217 of jaw closure bar 216 and coupling tip 156c of jaw pusher tube 156 may have a dovetail-type configuration or the like.

With continued reference to FIGS. 3 and 9-13, shaft assembly 210 includes a clip pusher bar 218 slidably supported within outer tube 212, adjacent jaw closure bar 216. Clip pusher bar 218 includes a proximal end portion 218a defining a proximal coupling 218c, and a distal end portion 218b defining a distal coupling 218d configured to engage and act on a cartridge clip pusher bar 304 of clip cartridge assembly 300, as will be described in greater detail below. Proximal coupling 218c of clip pusher bar 218 is configured to selectively connect to coupling tip 152b of clip pusher bar 150 of drive assembly 120 of handle assembly 100. In use, with proximal coupling 218c of clip pusher bar 218 connected to coupling tip 152b of clip pusher bar 150, axial translation of clip pusher bar 150 of handle assembly 100 results in axial translation of clip pusher bar 218 of endoscopic assembly 200. It is contemplated that proximal coupling 218c of clip pusher bar 218 and coupling tip 152b of clip pusher bar 150 may have a dovetail-type configuration of the like.

Shaft assembly 210 further includes a clip logic pusher or wedge plate 220 slidably supported within outer tube 212, and interposed between jaw closure bar 216 and clip pusher bar 218. Wedge plate 220 includes a proximal end portion 220a slidably connected to clip pusher bar 218, and a distal end portion 220b configured to engage and act on the pair of jaws 214, as will be described in greater detail below. A biasing member may be provided to urge wedge plate 220 to a distal position to spread the pair of jaws 214.

Turning now to FIGS. 1-3 and 15-22, clip cartridge assembly 300 of surgical clip applier 10 is shown. As mentioned above, clip cartridge assembly 300 is configured and dimensioned for elective loading into channel 212c formed in distal end portion 212b of outer tube 212 of endoscopic assembly 200, and is configured and dimensioned to selectively connect or couple to distal coupling 218d of clip pusher bar 218, as will be discussed in greater detail below.

Clip cartridge assembly 300 includes a clip tray 302 including base wall 302a, and a pair of spaced apart side walls or rails 302b supported on base wall 302b, with base wall 302a and side walls 302b defining a clip channel 302c. Clip tray 302 includes a linear array of distally extending resilient, deflectable fingers 302d projecting up from base wall 302a into clip channel 302c, at a location between side walls 302b.

Clip cartridge assembly 300 includes a cartridge clip pusher bar 304 slidably disposed adjacent clip tray 302. Cartridge clip pusher bar 304 includes a proximal end 304a defining a coupling stem, head or boss 304c configured to selectively connect with distal coupling 218d of clip pusher bar 218 of endoscopic assembly 200, and a distal end portion 304b defining a pusher 304d configured to engage a distal-most clip "C1" of a stack of clips "C" for loading the distal-most clip "C1" into the pair of jaws 214 of the endoscopic assembly 200.

Cartridge clip pusher bar 304 includes a linear array of distally oriented ramps 304e, with each ramp 304e defining a distal shoulder 304f. In an embodiment, the array of ramps 304e includes a pair of laterally spaced apart array of ramps defining a channel longitudinally therebetween. In use, when cartridge clip pusher bar 304 overlays or is adjacent to clip tray 302, deflectable fingers 302d of clip tray 302 is disposed between the pair of laterally spaced apart array of ramps 304e.

Clip cartridge assembly 300 includes a stack of surgical clips "C" interposed between clip tray 302 and cartridge clip pusher bar 304. The stack of surgical clips "C" are supported on or loaded in clip tray 302 such that an apex of each surgical clip "C" is disposed distal of a respective deflectable finger 302d of clip tray 302. Further, when cartridge clip pusher bar 304 is in a proximal position relative to clip tray 302, the pair of laterally spaced apart array of ramps 304e of cartridge clip pusher bar 304 is disposed proximal of a crown or of the legs of a respective surgical clip "C" of the stack of surgical clips.

Clip cartridge assembly 300 may be loaded with 10 surgical clips "C", or, in embodiments, clip cartridge assembly 300 may be loaded with any number of surgical clips C", provided clip cartridge assembly 300 and endoscopic assembly 200 are appropriately configured and dimensioned. Surgical clips "C" may be fabricated from materials know by those skilled in the art, including and not limited to stainless steel, titanium, or other metal alloys. In an embodiment it is contemplated that at least a final surgical clip of the stack of surgical clips "C" may be dyed a particular color to indicate to the user when a final surgical clip of clip cartridge assembly 300 is loaded into the pair of jaws 214.

Clip cartridge assembly 300 includes a cover 306 configured for connection to and support on clip tray 302. Cover 306 includes a series of resilient, deflectable fingers 306a projecting therefrom, and projecting towards cartridge pusher bar 304. Fingers 306a of cover 306 function to bias cartridge clip pusher bar 304 towards clip tray 302, and to maintain the stack of surgical clips "C" in sliding contact with base wall 302b of clip tray 302.

Cover 306 defines a window 306b formed in a proximal region thereof for access to a release button 304g of cartridge clip pusher bar 304. In use, with coupling boss 304c of cartridge clip pusher bar 304 coupled to distal coupling 218d of clip pusher bar 218 of endoscopic assembly 200, a user may press on release button 304g to disengage coupling boss 304c from complementary distal coupling 218d of clip pusher bar 218 (e.g., depress coupling boss 304c from within distal coupling 218d), and thus to disconnect clip cartridge assembly 300 from endoscopic assembly 200.

Figure 21:
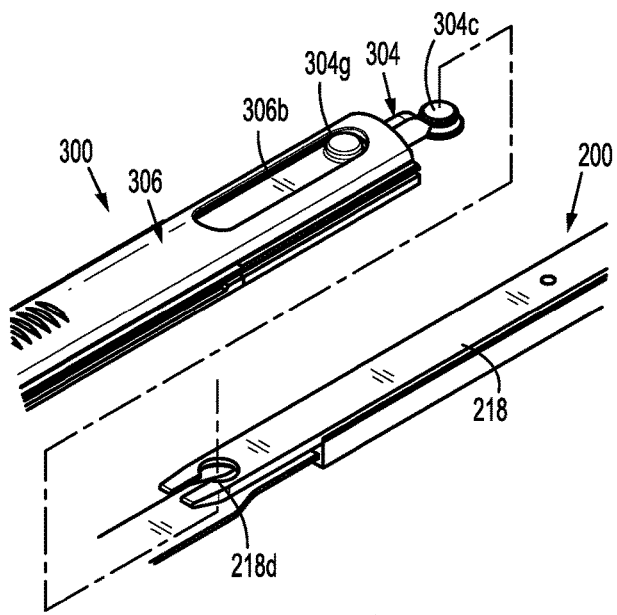
FIG. 21 is a perspective view illustrating a loading of the clip cartridge assembly to or with the shaft assembly, with an outer tube removed from the shaft assembly.
Figure 22:
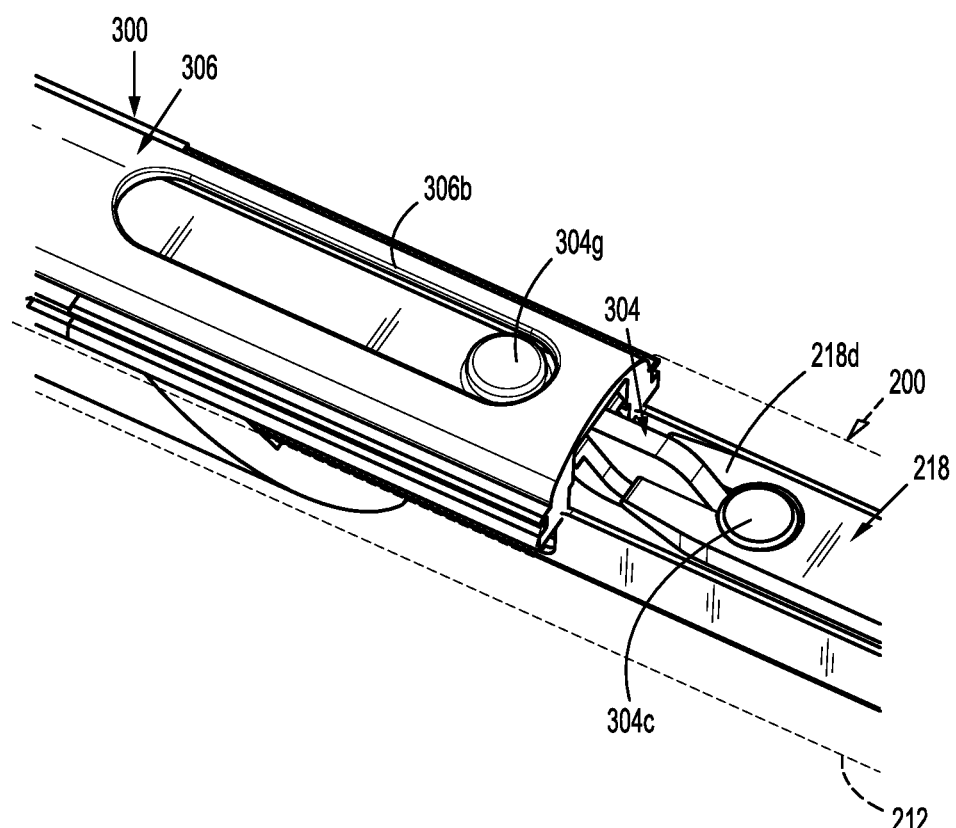
FIG. 22 is a perspective view illustrating the coupling of the clip pusher of the clip cartridge assembly with the clip pusher assembly of the shaft assembly.

With reference to FIGS. 20-22, a loading of clip cartridge assembly 300 to endoscopic assembly 200 is provided. In order to load clip cartridge assembly 300 into channel or window 212c of outer tube 212 of endoscopic assembly 200, a user depresses release button 304g of cartridge clip pusher bar 304 (in the direction of arrow "A" of FIG. 20). With release button 304g of cartridge clip pusher bar 304 depressed, coupling boss 304c of cartridge clip pusher bar 304 is inserted into outer tube 212 of endoscopic assembly 200 until coupling boss 304c of cartridge clip pusher bar 304 is in registration with distal coupling 218d of clip pusher bar 218 of endoscopic assembly 200. With coupling boss 304c of cartridge clip pusher bar 304 in registration with distal coupling 218d of clip pusher bar 218 of endoscopic assembly 200, release button 304g of cartridge clip pusher bar 304 may be released such that coupling boss 304c of cartridge clip pusher bar 304 enters into and mates with complementary distal coupling 218d of clip pusher bar 218 of endoscopic assembly 200. In so doing, clip cartridge assembly 300 is loaded into channel or window 212c of outer tube 212 of endoscopic assembly 200, and cartridge clip pusher bar 304 of clip cartridge assembly 300 is coupled to clip pusher bar 218 of endoscopic assembly 200.

As shown in FIGS. 2 and 10, channel or window 212c of outer tube 212 of endoscopic assembly 200 may be provided with lips or wings 212d extending along side edges thereof and extending towards one another to snap over or otherwise engages lateral sides of clip cartridge assembly 300 and further assist in maintaining clip cartridge assembly 300 loaded in endoscopic assembly 200.

Figure 15A:
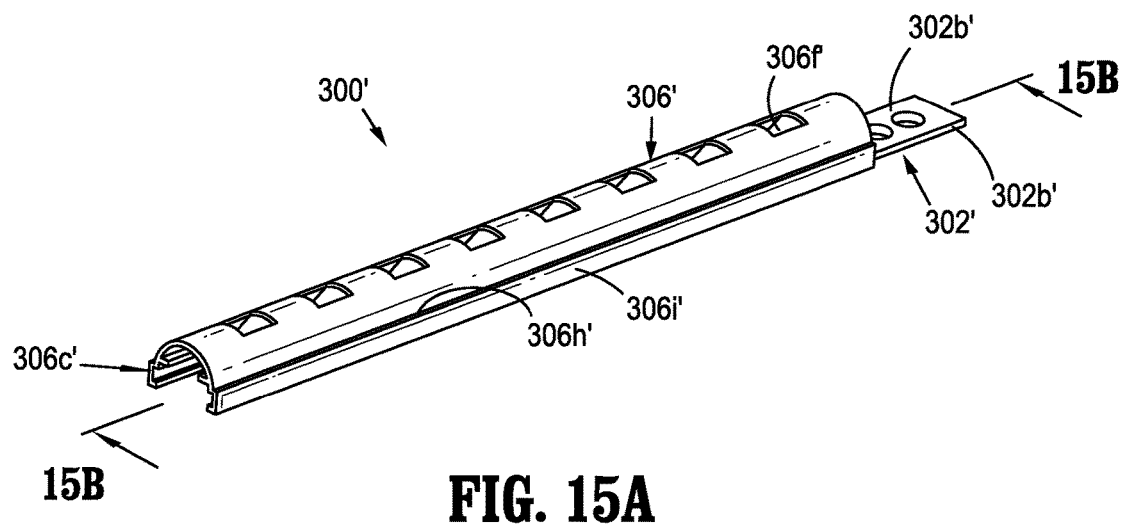
FIG. 15A is a perspective view of an alternate embodiment of the surgical clip cartridge assembly of FIG. 15.
Figure 15B:
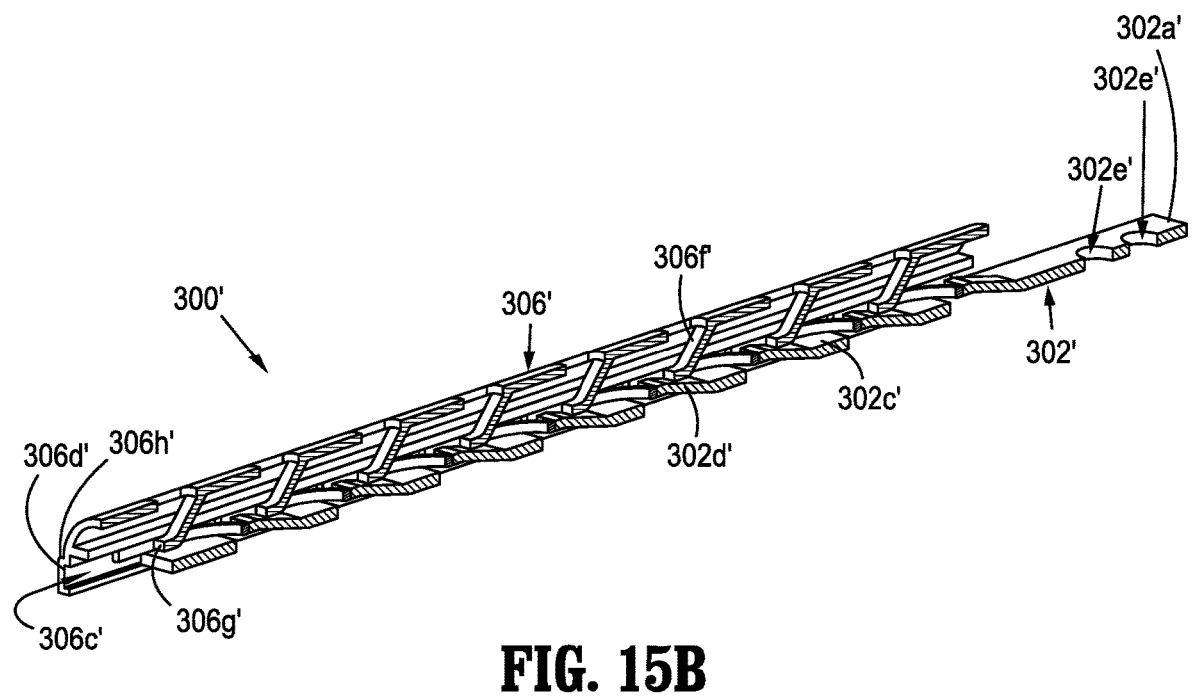
FIG. 15B is a cross-sectional view of the surgical clip cartridge assembly of FIG. 15A, taken along line 15B-15B of FIG. 15A.
Figure 16A:
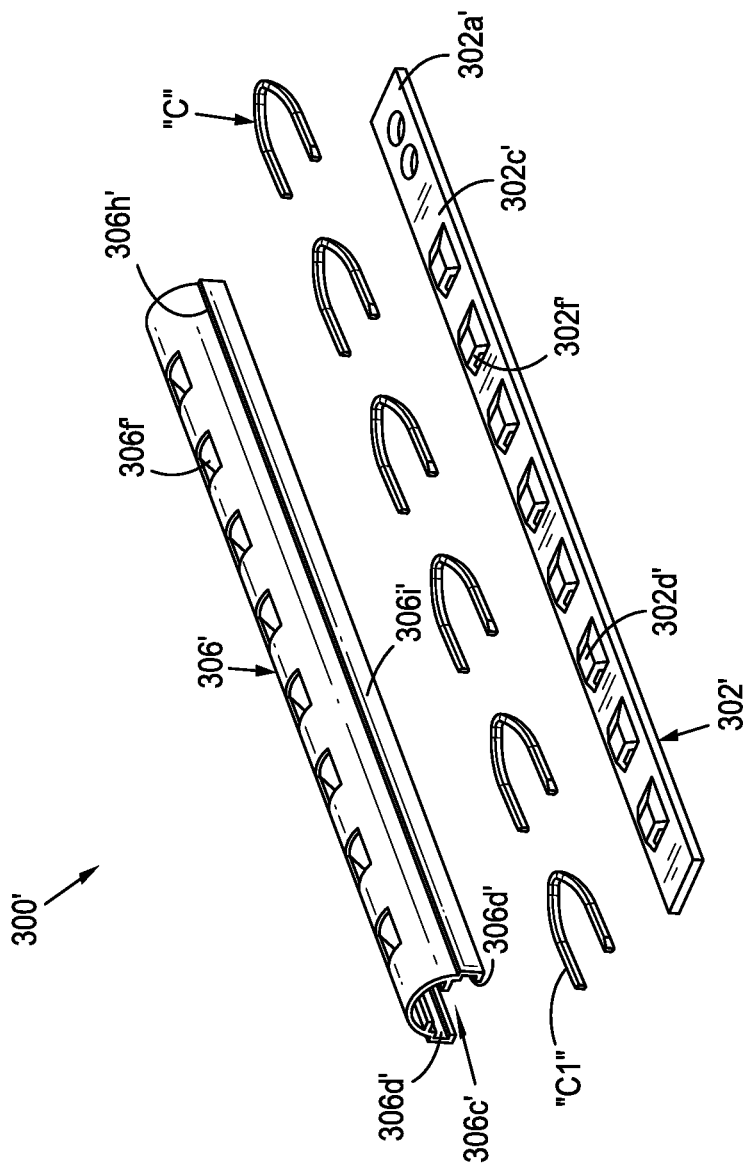
FIG. 16A is a perspective view, with parts separated, of the clip cartridge assembly of FIG. 15A.

With reference to FIGS. 15A, 15B, and 16A, an alternate embodiment of a clip cartridge assembly, provided in accordance with the present disclosure, is illustrated and generally identified by reference numeral 300'.

Similarly to clip cartridge assembly 300, clip cartridge assembly 300' is configured and dimensioned for selective loading into channel 212c formed in distal end portion 212b of outer tube 212 of endoscopic assembly 200, and is configured and dimensioned to selectively connect or couple to an alternate embodiment of distal coupling 218d of clip pusher bar 218, generally identified as distal coupling 218d' (FIG. 22A), as will be described in greater detail below.

Clip cartridge assembly 300' includes a clip tray 302' including a base wall 302a' defining a generally planar surface extending between opposed sides 302b'. Clip tray 302' includes a linear array of distally extending resilient, deflectable fingers 302d' projecting up from base wall 302a' at a location between opposed sides 302b'. Each resilient finger 302d' defines a distal shoulder 302f. In embodiments, distal shoulder 302f includes an arcuate profile corresponding to the shape of the crown of each clip "C" of the stack of clips in order to provide a more positive engagement therewith. Clip tray 302' includes a plurality of through holes 302e' defined through base wall 302a' at a proximal end thereof. Each one of the plurality of through holes 302e' is configured to releasably engage distal coupling 218d' of clip pusher bar 218 (FIG. 22A), as will be described in greater detail below.

In this manner, clip tray 302' of clip cartridge assembly 300' is utilized to load a distal most clip "C1" and advance each clip "C" of the stack of clips in lieu of cartridge clip pusher bar 304 of clip cartridge assembly 300. By removing clip cartridge pusher bar 304, the number of parts and overall complexity of clip cartridge assembly 300' is reduced.

Clip cartridge assembly 300' includes a cover 306' configured for connection to and support on outer tube 212 of endoscopic assembly 200. Clip cartridge assembly 300' includes a U-shaped channel 306c' defined therein and extending from a proximal end to a distal end thereof. U-shaped channel 306c' includes a pair of opposed slots 306d' defined in sidewalls 306e' thereof. Opposed slots 306d' are configured and dimensioned to slidably receive clip tray 302' therein. In this manner, cover 306' is formed from a suitable resilient material capable of being temporarily deformed to receive clip tray 302' therein, but maintain its original shape once any external force is no longer applied thereto. Cover 306' includes a linear array of distally oriented resilient, deflectable fingers 306f, with each resilient finger 306f defining a distal shoulder 306g'. In embodiments, the array of resilient fingers 306f includes a pair of laterally spaced apart array of resilient fingers defining a channel longitudinally therebetween. As can be appreciated, the resilient fingers 306f of cover 306' may function to bias clip tray 302' in a downward direction to ensure clip tray 302' may only travel in a longitudinal direction (i.e., inhibit vertical motion of clip tray 302').

A pair of opposed ridges 306h' are disposed on outer surface 306i' of cover 306' and are configured and dimensioned to releasably engage lips or wings 212d of outer tube 212 of endoscopic assembly 200, similarly as described above with respect to clip cartridge assembly 300 above.

Clip cartridge assembly 300' includes a stack of surgical clips interposed between clip tray 302' and cover 306' such that the surgical clips "C" are also disposed within the pair of opposed slots 306d' along with clip tray 302'. The stack of surgical clips are supported on or loaded in clip tray 302' such that an apex or crown of each surgical clip "C" is disposed distal of a respective deflectable finger 302d' of clip tray 302'. Further, when cover 306' is slidably connected to clip tray 302', each resilient finger 306f of the linear array of distally oriented resilient, deflectable fingers 306f is disposed proximal of a crown or the legs of a respective surgical clip "C" of the stack of surgical clips. In this manner, cover 306' slidably retains both the stack of surgical clips and clip tray 302' within the pair of opposed slots 306d'.

Clip cartridge assembly 300' may be loaded with 10 surgical clips "C", or in embodiments, clip cartridge assembly 300' may be loaded with any number of surgical clips "C", provided clip cartridge assembly 300' and endoscopic assembly 200 are appropriately configured and dimensioned. Surgical clips "C" are identical to those described above with respect to clip cartridge assembly 300, and therefore, a detailed description thereof will not be described herein in the interest of brevity.

Figure 22A:
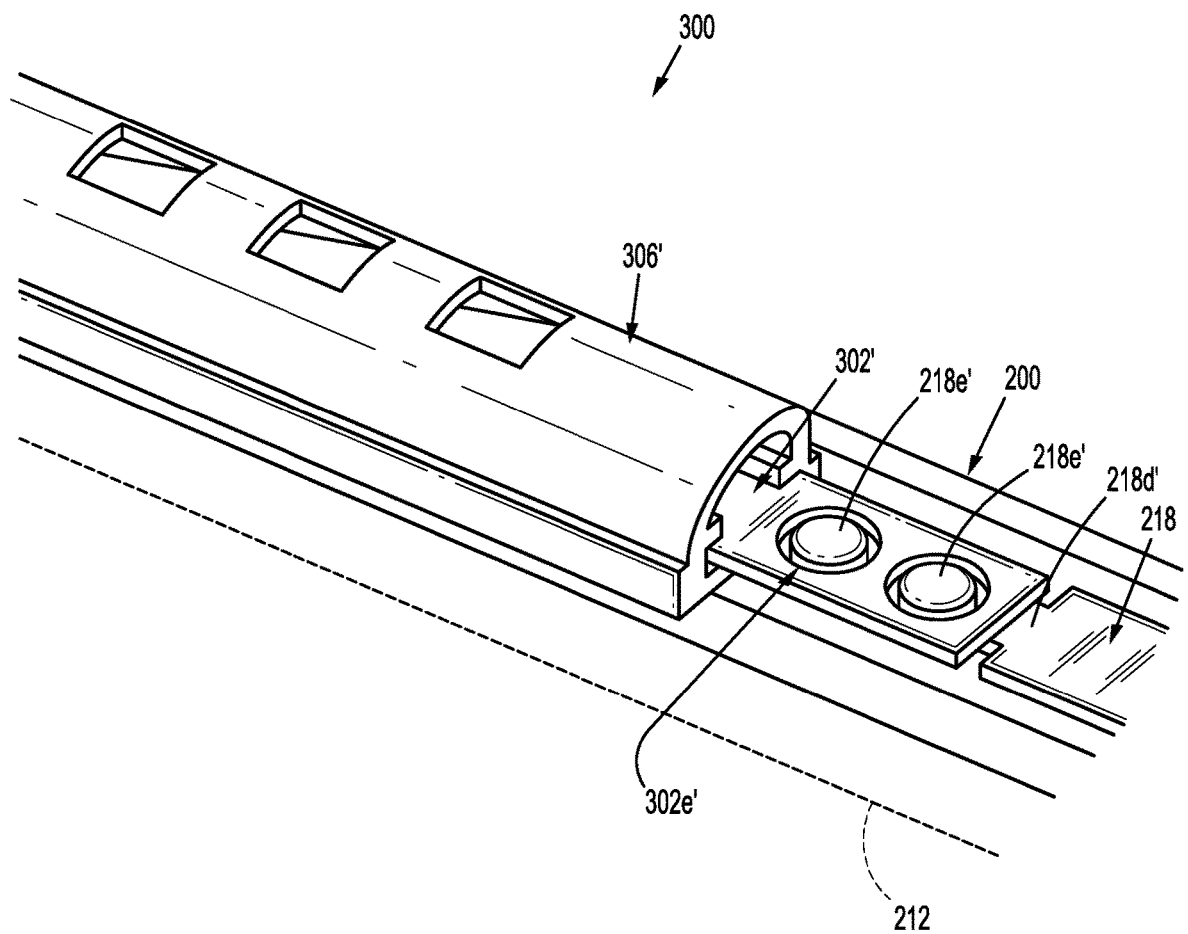
FIG. 22A is a perspective view illustrating the clip pusher of the clip cartridge assembly of FIG. 15A associated with an alternate clip pusher assembly of the shaft assembly.
Figure 23:
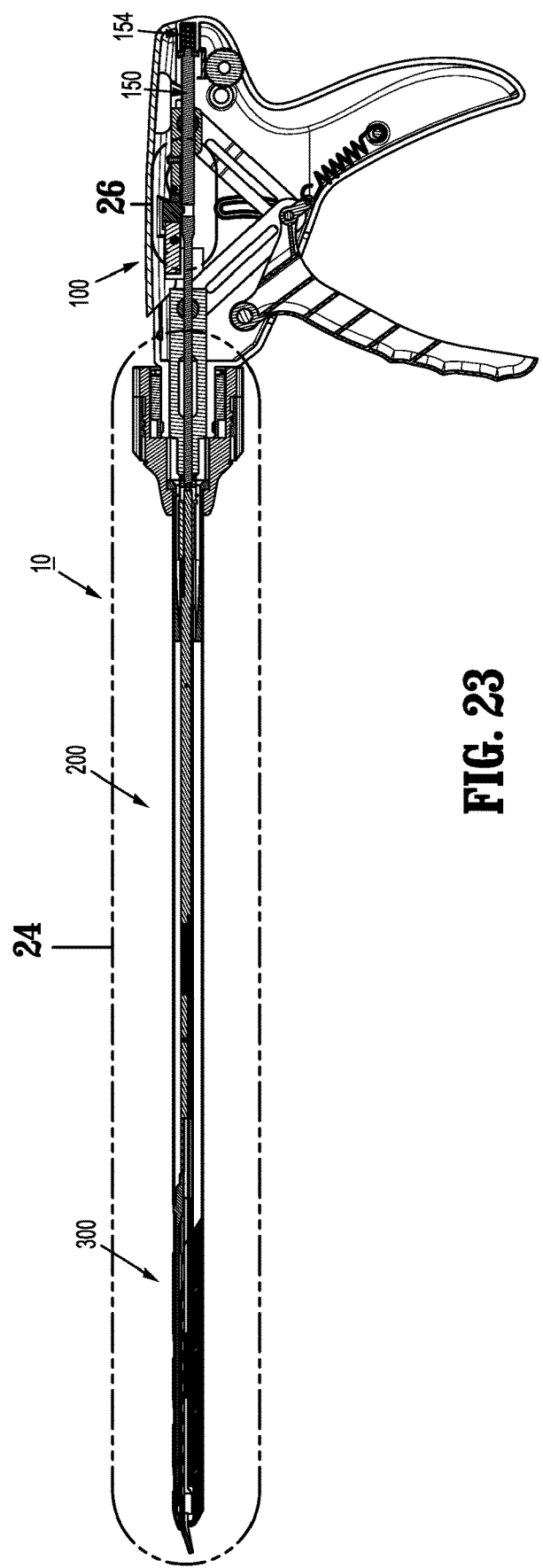
FIG. 23 is a longitudinal, cross-sectional view of the surgical clip applier of FIG. 1, as taken through 23-23 of FIG. 1, illustrating the clip applier in an un-actuated condition.
Figure 24:
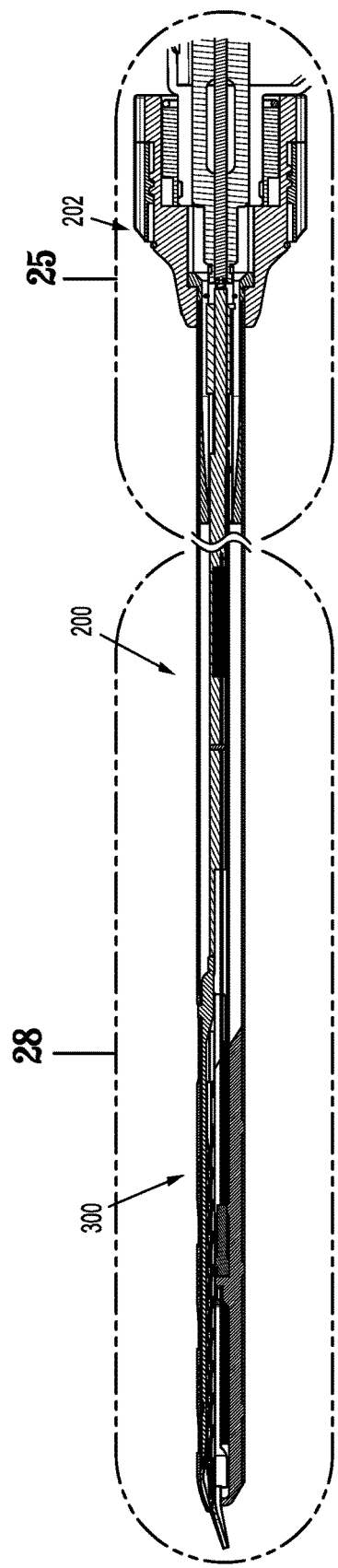
FIG. 24 is an enlarged view of the indicated area of detail of FIG. 23.
Figure 25:
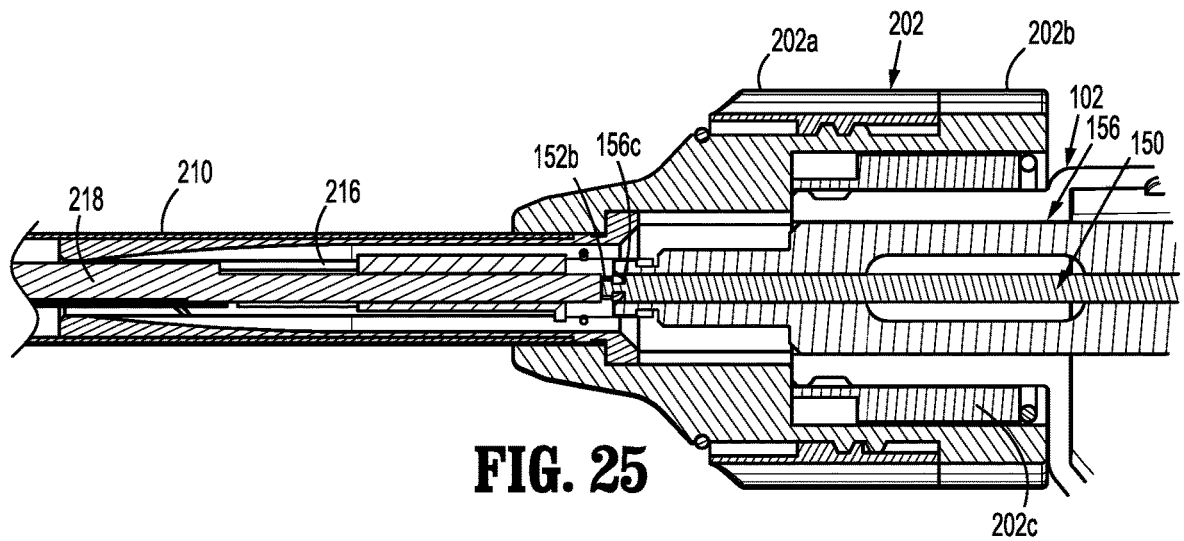
FIG. 25 is an enlarged view of the indicated area of detail of FIG. 24, illustrating a coupling of the shaft assembly to the handle assembly.
Figure 26:
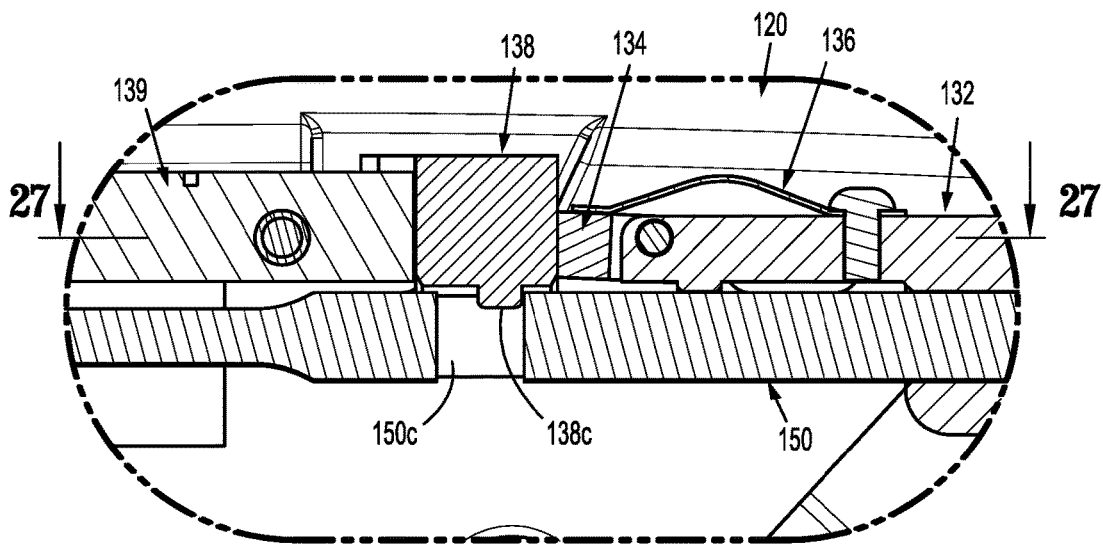
FIG. 26 is an enlarged view of the indicated area of detail of FIG. 23, illustrating a lock out of a clip pusher bar.
Figure 27:
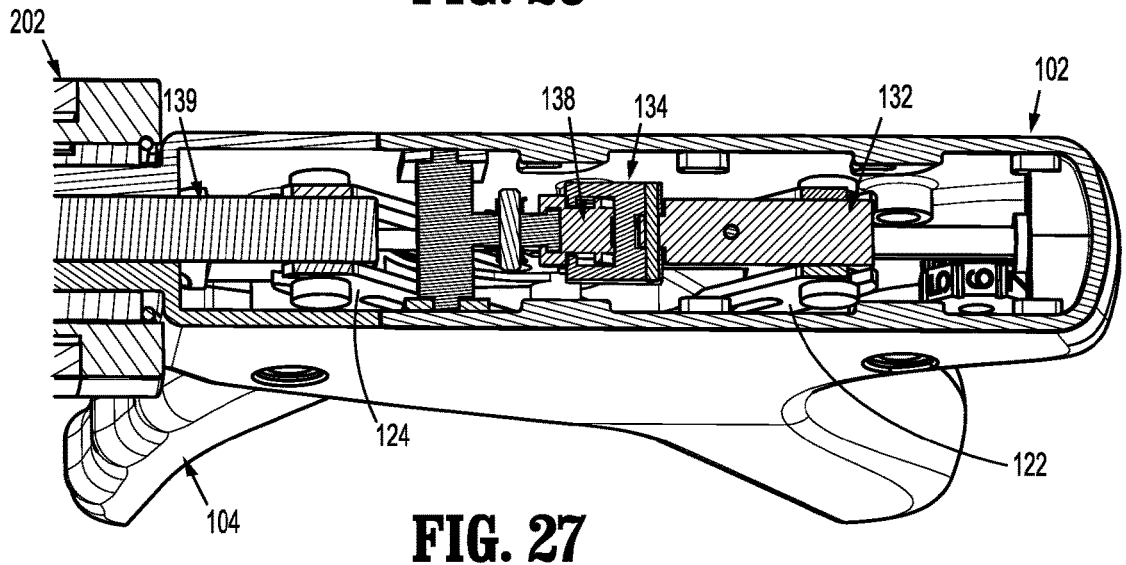
FIG. 27 is a cross-sectional view of the drive assembly of FIGS. 7 and 8, as taken through 27-27 of FIG. 26.
Figure 28:
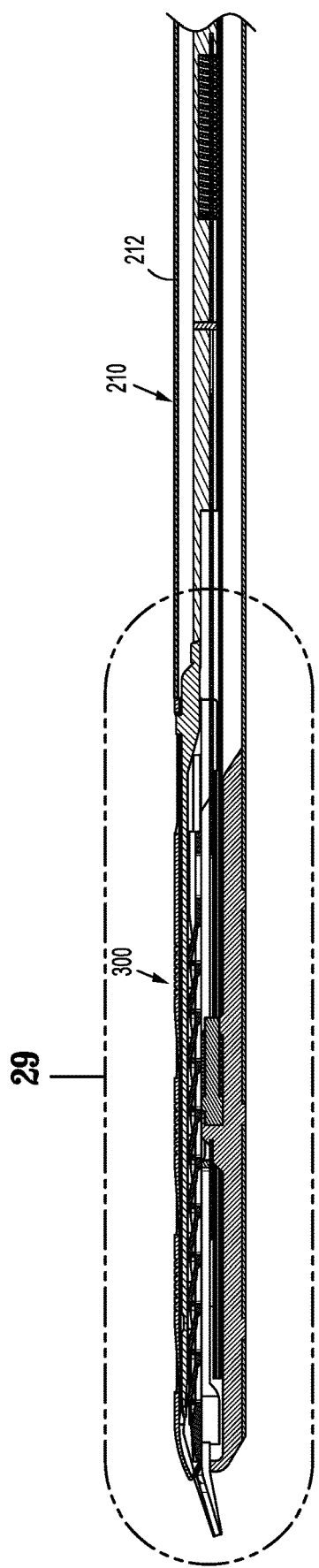
FIG. 28 is an enlarged view of the indicated area of detail of the shaft assembly illustrated in FIG. 24.

With additional reference to FIG. 22A, a loading of clip cartridge assembly 300' to endoscopic assembly 200 is provided. In order to load clip cartridge assembly 300' into channel or window 212c of outer tube 212 of endoscopic assembly 200, a user engages a pair of bosses 218e' or release buttons disposed on distal coupling 218d of clip pusher bar 218 of endoscopic assembly 200 with each respective through hole 302e' of clip tray 302'. It is contemplated that the pair of bosses 218e' may be constructed of a resilient material, such that a user may depress each boss 218e' of the pair of bosses 218e' to releasably engage each respective through hole 302e' of clip tray 302'. At this point, clip cartridge 300' is depressed into channel or window 212c of outer tube 212 of endoscopic assembly 200 such that the lips or wings 212d of endoscopic assembly 200 releasably engage the pair of opposed ridges 306h' of cover 306'. As can be appreciated, lips or wings 212d may releasably engage the pair of opposed ridges 306h' by means of a snap fit configuration.

With continued reference to FIGS. 1-22, and with additional specific reference to FIGS. 23-38, an exemplary mode of operation of clip applier 10 is shown and described. As shown in FIGS. 23-29, clip applier 10 is illustrated with endoscopic assembly 200 connected to handle assembly 100 (as described above), and with clip cartridge assembly 300 loaded in endoscopic assembly 200 (as described above).

Specifically, with trigger 104 of handle assembly in an unactuated condition, clip pusher bar 150 of handle assembly 100, clip pusher bar 218 of endoscopic assembly 200, and cartridge clip pusher bar 304 of clip cartridge assembly 300 are in an unactuated or proximal-most position. As so positioned, lock tab 138c of distal unlock member 138 of drive assembly 120 is disposed within window or slot 150c of clip pusher bar 150, thereby maintaining clip pusher bar 150 in the unactuated or proximal-most position, and maintaining biasing member 154 compressed between housing 102 of handle assembly 100 and flange 152a of clip pusher bar 150.

Additionally, with trigger 104 of handle assembly in an unactuated condition, distal shoulders 304f of distally oriented ramps 304e of cartridge clip pusher bar 304 of clip cartridge assembly 300 are disposed proximal of respective surgical clips of the stack of surgical clips "C".

Further, with trigger 104 of handle assembly in an unactuated condition, wedge plate 220 of endoscopic assembly 200 is maintained in an unactuated or proximal-most position.

With continued reference to FIGS. 1-28, and with additional specific reference to FIGS. 30-38, a firing stroke of surgical clip applier 10 is shown and described below. With clip cartridge assembly 300 loaded in endoscopic assembly 200, as trigger 104 of handle assembly 100 is actuated to a fully actuated position, a distal-most clip "C1" of the stack of surgical clips "C" is loaded into and formed by the pair of jaws 214 of endoscopic assembly 200.

Figure 30:
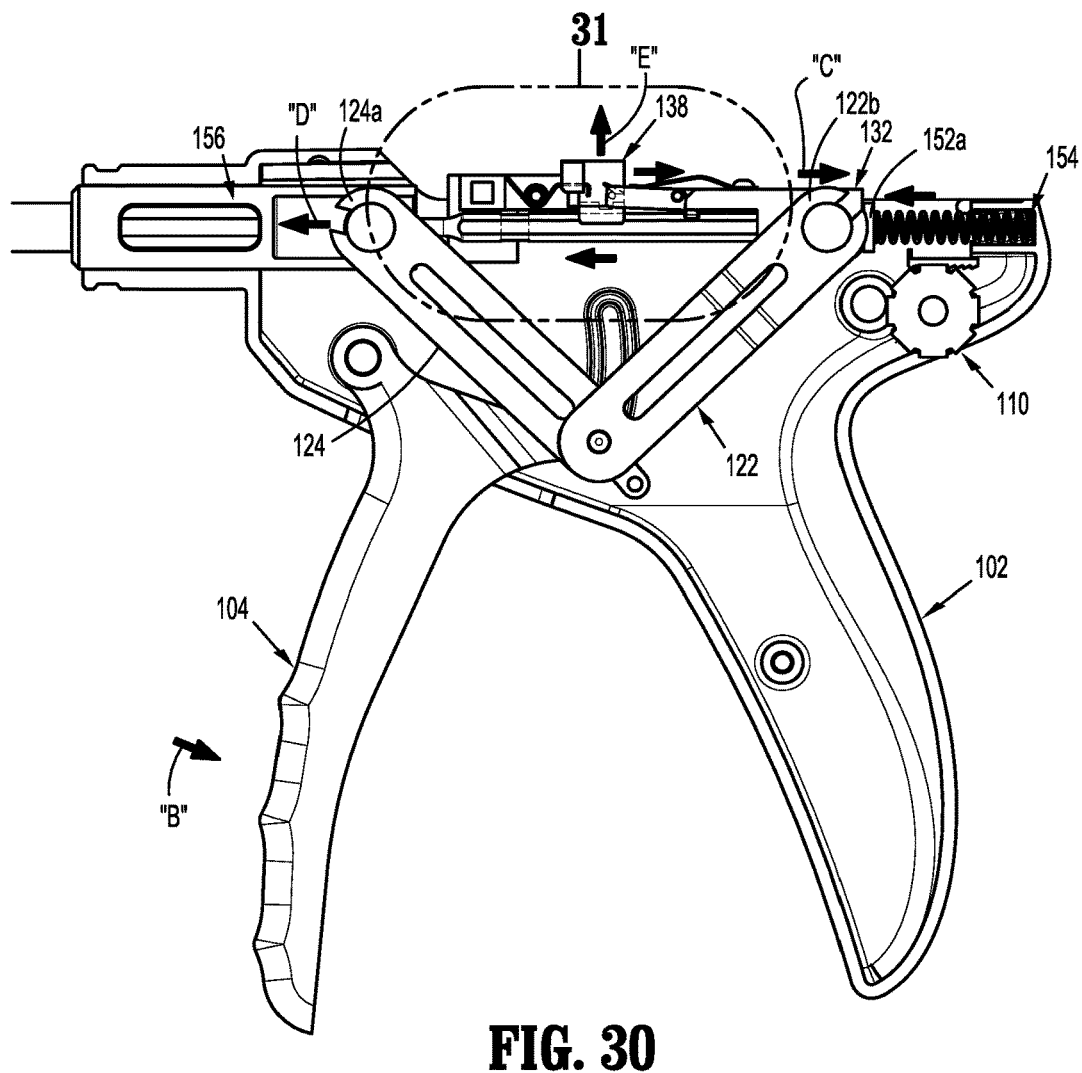
FIG. 30 is an elevational view of the handle assembly illustrated in FIG. 5, illustrating an initial actuation of the trigger.
Figure 31:
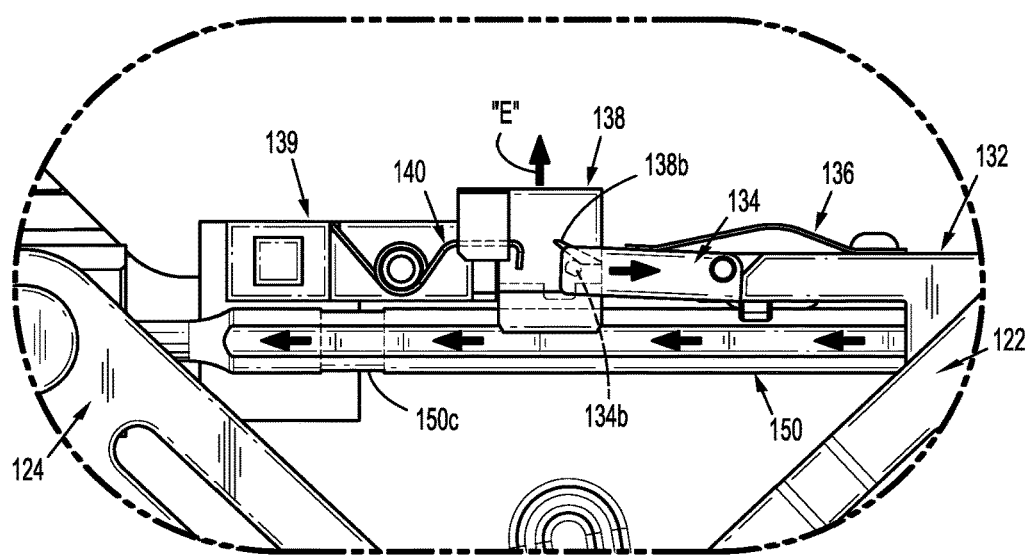
FIG. 31 is an enlarged view of the indicated area of FIG. 30, illustrating an unlocking of the clip pusher bar.

More specifically, as trigger 104 is actuated, in the direction of arrow "B" of FIG. 30, trigger 104 acts on proximal linkage 122 to move proximal coupling portion 122b of proximal linkage 122 in a proximal direction (as indicated by arrow "C" of FIG. 30), and acts on distal linkage 124 to move distal coupling portion 124a of distal linkage 124 in a distal direction (as indicated by arrow "D" of FIG. 30).

As proximal coupling portion 122b of proximal linkage 122 is moved in a proximal direction, proximal linkage 122 acts on guide block 132 of drive assembly 120 to move guide block 132, and in turn proximal unlock member 134, in a proximal direction. As proximal unlock member 134 is moved in a proximal direction, cam pins 134b of proximal unlock member 134 are moved into engagement with cam ramps 138b of distal unlock member 138 to urge distal unlock member 138 away from clip pusher bar 150 of handle assembly 100, in the direction of arrow "E" of FIGS. 30 and 31. As distal unlock member 138 is urged away from clip pusher bar 150, as soon as lock tab 138c of distal unlock member 138 clears window or slot 150c of clip pusher bar 150 thereby allowing biasing member 154 to expand and drive clip pusher bar 150 distally until flange 152a of clip pusher bar 150 abuts against guide block 132. Once cam pins 134b of proximal unlock member 134 are moved distally beyond cam ramps 138b of distal unlock member 138, biasing member 140 urges distal unlock member 138 back towards clip pusher bar 150 such that lock tab 138c of distal unlock member 138 contacts a surface of clip pusher bar 150, while still allowing clip pusher bar 150 to move in a distal direction.

As clip pusher bar 150 of handle assembly 100 is move in a distal direction, clip pusher bar 150 moves clip pusher assembly 218 of endoscopic assembly 200 in a distal direction, which in turn, acts on cartridge clip pusher bar 304 of clip cartridge assembly 300 to move cartridge clip pusher bar 304 in a distal direction to load a surgical clip "C" into the pair of jaws 214.

Additionally, as shown in FIGS. 32 and 33, as clip pusher assembly 218 of endoscopic assembly 200 (FIGS. 13 and 29) is moved in a distal direction, clip pusher assembly 218 acts on wedge plate 220 to move wedge plate 220 distally until distal end portion 220b of wedge plate 220 contacts camming wedge surfaces 214b of the pair of jaws 214 to either maintain the pair of jaws 214 in a spaced apart condition or the urge the pair of jaws 214 to a spaced apart condition. Specifically, distal end portion 220b of wedge plate 220 defines a pair of V-shaped notches 220c, one each of each of camming wedge surfaces 214b of the pair of jaws 214 to guide the pair of jaws 214 as wedge plate 220 is distally advanced.

With wedge plate 220 urging the pair of jaws 214 apart, as clip pusher bar 150 is moved in a distal direction, clip pusher bar 150 moves clip pusher assembly 218 of endoscopic assembly 200 in a distal direction, which, in turn, as shown in FIGS. 34 and 35, moves cartridge clip pusher bar 304 of clip cartridge assembly 300 in a distal direction to load distal-most clip "C1" of the stack of clips "C" in a distal direction and into the pair of jaws 214. Specifically, pusher 304d of cartridge clip pusher bar 304 engages the backspan of distal-most clip "C1" and pushes distal-most clip "C1" out of clip cartridge assembly 300 and into channel 214a of the pair of jaws 214. Additionally, and simultaneously with a distal movement of the distal-most clip "C1", as cartridge clip pusher bar 304 of clip cartridge assembly 300 moves in a distal direction, distal shoulders 304f of ramps 304e of cartridge clip pusher bar 304 abut against a respective backspan of a respective surgical clip of the remaining surgical clips "C" to also urge the remaining surgical clips "C" in a distal direction. Cartridge clip pusher bar 304 distally advances the remaining surgical clips "C" until each remaining surgical clip "C" is advanced distally past a next adjacent resilient, deflectable finger 302d of clip cartridge assembly 300.

After, flange 152a of clip pusher bar 150 abuts against guide block 132, as trigger 104 is actuated further, proximal linkage 122 continues to move guide block 132 in a proximal direction, and guide block 132 acts on flange 152a of clip pusher bar 150 to urge clip pusher bar 150 in a proximal direction. As clip pusher bar 150 is moved in a proximal direction, clip pusher bar 150 pulls or moves clip pusher assembly 218 of endoscopic assembly 200 in a proximal direction, which, in turn pulls or moves cartridge clip pusher bar 304 of clip cartridge assembly 300 in a proximal direction. As cartridge clip pusher bar 304 is moved in a proximal direction, ramps 304e of cartridge clip pusher bar 304 abut against a distal surface of the backspans of the remaining surgical clips "C" to also urge the remaining surgical clips "C" in a proximal direction. Cartridge clip pusher bar 304 proximally retracts the remaining surgical clips "C" until each remaining surgical clip "C" is retracted into contact with a respective distal tip of a respective resilient, deflectable finger 302d of clip cartridge assembly 300, which blocks or stops further proximal retraction of the remaining surgical clips "C".

As clip pusher bar 150 of handle assembly 100 continues to be urged in a proximal direction by guide block 132, as window or slot 150c of clip pusher bar 150 comes into registration with lock tab 138c of distal unlock member 138, biasing member 140 urges lock tab 138c of distal unlock member 138 back into window or slot 150c of clip pusher bar 150.

As mentioned above, as trigger 104 is actuated, in the direction of arrow "B" of FIG. 30, trigger 104 also acts on distal linkage 124 to move distal coupling portion 124a of distal linkage 124 in a distal direction (as indicated by arrow "D" of FIG. 30). As distal coupling portion 124a of distal linkage 124 is moved in a distal direction, distal coupling portion 124a urges jaw pusher tube 156 in a distal direction. With jaw pusher tube 156 connected to jaw closure bar 216 of endoscopic assembly 200 (as described above), as jaw pusher tube 156 is moved in a distal direction jaw closure bar 216 is also moved in a distal direction. With reference to FIGS. 36 and 37, as jaw closure bar 216 is moved in a distal direction, channel 216c of jaw closure bar 216 (see FIGS. 11 and 12) receives or otherwise engages the pair of camming wedge surfaces 214b of the pair of jaws 214 to move the pair of jaws to the closed or approximated position.

With a distal-most surgical clip "C1" loaded in the pair of jaws 214, as jaw closure bar 216 moves the pair of jaws to the closed or approximated position, distal-most surgical clip "C1" is formed therebetween, for example, on a vessel "V" or the like, as shown in FIG. 38.

A timing of the actuation of clip applier 10 is such that pusher 304d of cartridge clip pusher bar 304 of clip cartridge assembly 300 is withdrawn from between the pair of jaws 214 of endoscopic assembly 200 prior to jaw closure bar 216 engaging the pair of camming wedge surfaces 214b of the pair of jaws 214.

With a surgical clip "C" formed, trigger 104 may be released and returned to an unactuated position either by or with the assistance of trigger return spring 104a (see FIGS. 4 and 5). As trigger 104 is returned to an unactuated position, trigger 104 acts on proximal linkage 122 to move guide block 132 in a distal direction, and acts on distal linkage 124 to move jaw pusher tube 156 in a proximal direction, thereby resetting clip applier 10 for another firing.

It is contemplated that handle assembly 100 may include, as shown in FIGS. 4, 5 and 30, a counter mechanism 110, configured and adapted to decrement an indicia thereon with each firing of surgical clip applier 10. In this manner, a user may keep track of the number of surgical clips remaining in the clip cartridge assembly 300.

In use, surgical clip applier 10, as mentioned above, is capable of loading different surgical clip cartridge assemblies 300 in endoscopic assembly 200. Specifically, endoscopic assembly 200 may be loaded with a surgical clip cartridge assembly 300 that is loaded with a stack of surgical clips "C" having a first size, or endoscopic assembly 200 may be loaded with a surgical clip cartridge assembly 300 that is loaded with a stack of surgical clips "C" having a second size different than the first size.

In this manner, the user or surgeon may load a surgical clip cartridge assembly 300, loaded with a particular size of surgical clips, depending on the particular surgical procedure to be performed. Additionally, during a surgical procedure, if the need arises to use a different sized surgical clip, the user or surgeon may eject or unload the surgical clip cartridge assembly 300 that is loaded in endoscopic assembly 200 and then load a new surgical clip cartridge assembly 300 (having a different sized stack of surgical clips loaded therein as compared to the unloaded surgical clip cartridge assembly 300) into endoscopic assembly 200.

In accordance with the present disclosure, it is contemplated that surgical clip applier 10 includes a reusable and sterilizable handle assembly 100 that may be used for multiple surgical procedures; a reusable and sterilizable endoscopic assembly 200 that may also be used for multiple surgical procedures; and a disposable, single use clip cartridge assembly 300 (e.g., wherein the clip cartridge assembly 300 is disposed of when unloaded from endoscopic assembly 200). It is contemplated that endoscopic assembly 200 may be disposed of following the particular surgical procedure and not reused or sterilized.

Also in accordance with the present disclosure, it is further contemplated that a surgical kit may be provided including a single handle assembly 100, a single endoscopic assembly 200, and a plurality of clip cartridge assemblies 300 including at least a first set of clip cartridge assemblies loaded with a stack of surgical clips having a first size and a second set of clip cartridge assemblies loaded with a stack of surgical clips having a second size different than the first size. The kit may include instructions for the assembly or surgical clip applier 10, the use of surgical clip applier 10, and the processing of surgical clip applier assembly 10 following use.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A reposable surgical clip applier, comprising:
   an endoscopic assembly selectively connectable to a distal end of a drive assembly, the endoscopic assembly including:
      an outer tube defining a window in a distal end portion of the outer tube;
      a mounting tooth projecting radially inward from the outer tube;

a pair of jaws selectively supported in the window of the outer tube and extending from a distal end of the outer tube, wherein the pair of jaws define a window formed in a shank portion of the pair of jaws, wherein the mounting tooth is located within the window defined in the pair of jaws, wherein the mounting tooth extends proximally to engage a surface of the pair of jaws and retain the pair of jaws within the window of the outer tube;

a biasing member acting on the pair of jaws to bias the pair of jaws in a distal direction, wherein the biasing member urges the pair of jaws into trapped engagement with the mounting tooth;

a jaw closure bar slidably supported within the outer tube, wherein a proximal end of the jaw closure bar is selectively operatively connectable to the distal end of the drive assembly, and wherein a distal end of the jaw closure bar is selectively engageable with the pair of jaws to close the pair of jaws upon a distal translation of the jaw closure bar relative to the pair of jaws, wherein the proximal end of the jaw closure bar is configured to receive distal and proximal axial actuating forces from the drive assembly; and a clip pusher bar slidably supported within the outer tube, wherein a proximal end of the clip pusher bar is selectively operatively connectable to the distal end of the drive assembly, and wherein a distal end of the clip pusher bar is configured for selective connection with a clip pusher bar of a clip cartridge assembly.

2. The reposable surgical clip applier according to claim 1, wherein the pair of jaws define:

a channel between the pair of jaws for receipt of a surgical clip within the channel; and a pair of camming wedge surfaces projecting therefrom and being configured for selective engagement by the jaw closure bar to actuate the pair of jaws to a closed position upon a distal advancement of the jaw closure bar.

3. A reposable surgical clip applier, comprising:

a handle assembly supporting a drive assembly defining a coupling tip at a distal end of the drive assembly;

an endoscopic assembly selectively connectable to the drive assembly of the handle assembly, the endoscopic assembly including:

an outer tube defining a window in a distal end portion of the outer tube;

a pair of jaws selectively supported in the window of the outer tube and extending from a distal end of the outer tube, wherein the pair of jaws define a window formed in a shank portion of the pair of jaws;

a mounting tooth projecting radially inward from the outer tube, wherein the mounting tooth is located within the window defined in the pair of jaws, wherein the mounting tooth extends proximally to engage a surface of the pair of jaws and retain the pair of jaws within the window of the outer tube;

a biasing member acting on the pair of jaws to bias the pair of jaws in a distal direction, wherein the biasing member urges the pair of jaws into trapped engagement with the mounting tooth;

a jaw closure bar slidably supported within the outer tube, wherein a proximal end of the jaw closure bar is selectively operatively connectable to the coupling tip of the drive assembly, and wherein a distal end of the jaw closure bar is selectively engageable with the pair of jaws to close the pair of jaws upon a distal translation of the jaw closure bar relative to the pair of jaws, wherein the proximal end of the jaw closure bar is configured to receive distal and proximal axial actuating forces from the drive assembly; and a clip pusher bar slidably supported within the outer tube, wherein a proximal end of the clip pusher bar is selectively operatively connectable to the drive assembly, and wherein a distal end of the clip pusher bar is configured for selective connection with a clip pusher bar of a clip cartridge assembly.

4. The reposable surgical clip applier according to claim 3, wherein the pair of jaws define:

a channel between the pair of jaws for receipt of a surgical clip within the channel; and a pair of camming wedge surfaces projecting therefrom and being configured for selective engagement by the jaw closure bar to actuate the pair of jaws to a closed position upon a distal advancement of the jaw closure bar.

5. The reposable surgical clip applier according to claim 4, wherein the handle assembly includes:

a housing; and a trigger pivotally supported on and extending from the housing, wherein the drive assembly is supported within the housing and is operatively actuatable by the trigger.

6. The reposable surgical clip applier according to claim 5, further comprising:

a clip cartridge assembly selectively loadable in the window defined within the outer tube of the endoscopic assembly, the clip cartridge assembly including:

a clip tray including a plurality of distally oriented, deflectable, resilient fingers projecting from a base wall thereof, each resilient finger of the clip tray terminating in a distal shoulder, a proximal end of the clip tray being configured for selective connection with the clip pusher bar of the endoscopic assembly of the reposable surgical clip applier;

a plurality of surgical clips disposed on the base wall of the clip tray, wherein each one of the plurality of surgical clips is disposed distally of each respective resilient finger of the clip tray; and a cover including a plurality of distally oriented, deflectable, resilient fingers projecting within a channel defined through proximal and distal ends of the cover, each resilient finger of the cover terminating in a distal shoulder, wherein the cover includes a pair of opposed slots defined within sidewalls of the channel, the pair of opposed slots configured to slidably retain the clip tray and the plurality of surgical clips therein, wherein each one of the plurality of surgical clips is disposed distally of each respective resilient finger of the cover.

7. The reposable surgical clip applier according to claim 6, wherein the endoscopic assembly includes:

a knob assembly configured and adapted for selective connection to the housing of the handle assembly, wherein the outer tube is supported on the knob assembly.

8. A reposable surgical clip applier, comprising:

an endoscopic assembly selectively connectable to a drive assembly, the endoscopic assembly including:

an outer tube defining a window in a distal end portion of the outer tube;

a pair of jaws selectively supported in the window of the outer tube and extending from a distal end of the outer tube, wherein the pair of jaws define a jaw window formed in a shank portion of the pair of jaws, wherein the shank portion integrally unites the pair of jaws;

a mounting tooth integrally formed in and projecting radially inward and proximally from the outer tube, wherein the mounting tooth is located within the jaw window defined in the pair of jaws;

a biasing member acting on the pair of jaws to bias the pair of jaws in a distal direction and into locking engagement with the mounting tooth;

a jaw closure bar slidably supported within the outer tube, wherein a proximal end of the jaw closure bar is selectively operatively connectable to the drive assembly, and wherein a distal end of the jaw closure bar is selectively engageable with the pair of jaws to close the pair of jaws upon a distal translation of the jaw closure bar relative to the pair of jaws; and a clip pusher bar slidably supported within the outer tube, wherein a proximal end of the clip pusher bar is selectively operatively connectable to the drive assembly, and wherein a distal end of the clip pusher bar is configured for selective connection with a clip pusher bar of a clip cartridge assembly.

\* \* \* \* \*